United States Patent
Michels et al.

(10) Patent No.: US 8,604,028 B2
(45) Date of Patent: Dec. 10, 2013

(54) FUROPYRIDINYL-SUBSTITUTED 1,4-DIHYDROPYRIDINE DERIVATIVES AND METHODS OF USE THEREOF

(75) Inventors: Martin Michels, Köln (DE); Hans Briem, Berlin (DE); Alexandros Vakalopoulos, Hilden (DE); Katja Zimmermann, Düsseldorf (DE); Nicole Teusch, Wülfrath (DE)

(73) Assignee: Bayer Intellectual Property GmbH, Monheim (DE)

( * ) Notice: Subject to any disclaimer, the term of this patent is extended or adjusted under 35 U.S.C. 154(b) by 0 days.

(21) Appl. No.: 13/510,483

(22) PCT Filed: Nov. 15, 2010

(86) PCT No.: PCT/EP2010/067506
§ 371 (c)(1),
(2), (4) Date: Oct. 9, 2012

(87) PCT Pub. No.: WO2011/061157
PCT Pub. Date: May 26, 2011

(65) Prior Publication Data
US 2013/0131055 A1    May 23, 2013

(30) Foreign Application Priority Data
Nov. 18, 2009 (EP) ..................... 09176331

(51) Int. Cl.
A61K 31/5383 (2006.01)
A61K 45/06 (2006.01)
C07D 498/04 (2006.01)
A61K 31/437 (2006.01)

(52) U.S. Cl.
USPC ................. 514/230.5; 546/115; 546/116

(58) Field of Classification Search
None
See application file for complete search history.

(56) References Cited

FOREIGN PATENT DOCUMENTS

EP         0217530 B1 *   4/1987

* cited by examiner

*Primary Examiner* — Bong-Sook Baek
*Assistant Examiner* — Taina D Matos Negron

(57) ABSTRACT

This invention relates to novel 4-(furo[3,2-c]pyridin-2-yl)-1,4-dihydropyridine derivatives having protein tyrosine kinase inhibitory activity, to a process for the manufacture thereof and to the use thereof for the treatment of c-Met-mediated diseases or c-Met-mediated conditions, particularly cancer and other proliferative disorders.

4 Claims, No Drawings

FUROPYRIDINYL-SUBSTITUTED 1,4-DIHYDROPYRIDINE DERIVATIVES AND METHODS OF USE THEREOF

This invention relates to novel 4-(furo[3,2-c]pyridin-2-yl)-1,4-dihydropyridine derivatives having protein tyrosine kinase inhibitory activity, to a process for the manufacture thereof and to the use thereof for the treatment of c-Met-mediated diseases or c-Met-mediated conditions, particularly cancer and other proliferative disorders.

Cancer is one of the most common widespread diseases. Over 4.4 million people worldwide were diagnosed with breast, colon, ovarian, lung or prostate cancer in 2002, and over 2.5 million people died of these devastating diseases (Globocan 2002 Report, http://www-dep.iarc.fr/globocan/down-loads.htm). In the United States alone, over 1.25 million new cases and over 500 000 deaths from cancer were predicted in 2005. The majority of these new cases were expected to be cancers of the colon (~100 000), lung (~170 000), breast (~210 000) and prostate (~230 000). Both the incidence and prevalence of cancer is predicted to increase by approximately 15% over the next ten years, reflecting an average growth rate of 1.4% (American Cancer Society, Cancer Facts and Figures 2005; http://www.cancer.org/docroot/STT/content/STT_1x_Cancer_Facts_Figures_2007.asp).

There are many ways how cancers can arise, which is one of the reasons why their therapy is difficult. One way is the transformation of cells by oncoproteins, which arise from normal cellular proteins by genetic mutations, which results in a non-physiological activation of these proteins. One family of proteins from which a number of oncoproteins derive are tyrosine kinases (e.g. src kinase) and in particular receptor tyrosine kinases (RTKs). In the past two decades, numerous avenues of research have demonstrated the importance of receptor tyrosine kinase (RTK)-mediated signalling in the regulation of mammalian cell growth. Recently, results have been achieved in the clinic with selective small-molecule inhibitors of tyrosine kinases as anti-tumourigenic agents.

The c-Met receptor also is a receptor tyrosine kinase. Its oncogenic potential was identified in the early 1980s, when a mutated Met was isolated from a chemically induced human osteosarcoma cell line which contained the kinase domain of the Met gene fused to a dimerization domain at its N-terminus [C. S. Cooper et al., *Nature* 311: 29-33 (1984)].

The cellular Met protein is a heterodimeric transmembrane protein synthesized as a single chain 190 kd precursor [G. A. Rodrigues et al., *Mol. Cell. Biol.* 11: 2962-70 (1991)]. The precursor is cleaved intracellularly after amino acid residue 307 to form the 50 kd α-chain and the 145 kd β-chain, which are connected by disulfide bridges. The α-chain is entirely extracellular, whereas the β-chain spans the plasma membrane. The β-chain is composed of an N-terminal sema domain, which together with the α-chain mediates ligand binding. The remainder of the ectodomain of the β-chain is composed of a cysteine-rich domain and four immunoglobulin domains and is followed by the transmembrane region and the intracellular domain. The intracellular domain contains a juxtamembrane domain, the kinase domain and a C-terminal domain, which mediates the downstream signalling. Upon ligand binding, a dimerization of the receptor is induced, and the kinase domain is activated by a cascade of tyrosine autophosphorylation steps in the juxtamembrane region (Y1003), the activation loop of the kinase (Y1234 and Y1235) and the carboxy-terminal domain (Y1349 and Y1356). Phosphorylated Y1349 and Y1356 comprise the multi-substrate docking site for binding adapter proteins necessary for downstream c-Met signalling [C. Ponzetto et al., *Cell* 77: 261-71 (1994)]. One of the most crucial substrates for c-Met signalling is the scaffolding adaptor protein Gab1, which binds to either Y1349 or Y1356 via an unusual phosphotyrosine binding site (termed mbs: met binding site) which causes a unique prolonged intracellular signal. Another important substrate is the adaptor protein Grb2. Depending on the cellular context, these adaptors mediate the activation of various intracellular signal pathways like the ones signalling via ERK/MAPK, PI3K/Akt, Ras, JNK, STAT, NFκB and β-catenin.

c-Met is uniquely activated by hepatocyte growth factor (HGF), also known as scatter factor, and its splice variants, which is its only known biologically active ligand [L. Naldini et al., *Oncogene* 6: 501-4 (1991)]. HGF has a distinct structure which reveals similarities to proteinases of the plasminogen family. It is composed of an amino-terminal domain followed by four kringle domains and a serine protease homology domain, which is not enzymatically active. Similar to c-Met, HGF is synthesized as an inactive single chain precursor (pro-HGF), which is extracellularly cleaved by serine proteases (e.g. plasminogen activators and coagulation factors) and converted into a disulfide-linked active α- and β-chain heterodimer. HGF binds heparan sulfate proteoglycans with high affinity, which keeps it mainly associated with the extracellular matrix and limits its diffusion. Crystal structure analyses indicate that HGF forms a dimer, which upon binding to c-Met induces dimerization of the receptor.

HGF is expressed by mesenchymal cells, and its binding to c-Met, which is widely expressed in particular in epithelial cells, results in pleiotropic effects in a variety of tissues including epithelial, endothelial, neuronal and hematopoetic cells. The effects generally include one or all of the following phenomena: i) stimulation of mitogenesis; HGF was identified by its mitogenic activity on hepatocytes; ii) stimulation of invasion and migration; in an independent experimental approach, HGF was identified as scatter factor based on its induction of cell motility ("scattering"); and iii) stimulation of morphogenesis (tubulogenesis). HGF induces the formation of branched tubules from canine kidney cells in a collagen matrix. Furthermore, evidence from genetically modified mice and from cell culture experiments indicate that c-Met acts as a survival receptor and protects cells from apoptosis [N. Tomita et al., *Circulation* 107: 1411-1417 (2003); S. Ding et al., *Blood* 101: 4816-4822 (2003); Q. Zeng et al., *J. Biol. Chem.* 277: 25203-25208 (2002); N. Horiguchi et al., *Oncogene* 21: 1791-1799 (2002); A. Bardelli et al., *Embo J.* 15: 6205-6212 (1996); P. Longati et al., *Cell Death Differ.* 3: 23-28 (1996); E. M. Rosen, *Symp. Soc. Exp. Biol.* 47: 227-234 (1993)]. The coordinated execution of these biological processes by HGF results in a specific genetic program which is termed as "invasive growth".

Under normal conditions, c-Met and HGF are essential for embryonic development in mice, in particular for the development of the placenta and the liver and for the directional migration of myoblasts from the somites of the limbs. Genetic disruption of the c-Met or HGF genes results in identical phenotypes which shows their unique interaction. The physiological role of c-Met/HGF in the adult organism is less well understood, but experimental evidence suggests that they are involved in wound healing, tissue regeneration, hemopoiesis and tissue homeostasis.

The identification of the oncoprotein TPR-MET was a first hint that c-Met may play a role in tumourigenesis. Additional substantial evidence is derived from a number of different experimental approaches. Overexpression of c-Met or HGF in human and murine cell lines induces tumouri-genicity and a metastatic phenotype when expressed in nude mice. Transgenic overexpression of c-Met or HGF induces tumourigenesis in mice.

Most intriguingly, missense mutations of c-Met or mutations which activate the receptor have been identified in sporadic and hereditary papillary kidney carcinomas (HPRC) as well as in other cancer types like lung, gastric, liver, head and neck, ovarian and brain cancers. Significantly, specific c-Met mutations in HPRC families segregate with disease, forming a causal link between c-Met activation and human cancer [L. Schmidt et al., *Nat. Genet.* 16: 68-73 (1997); B. Zbar et al., *Adv. Cancer Res.* 75: 163-201 (1998)]. Activation mutations with the strongest transforming activities are located in the activation loop (D1228N/H and Y1230H/D/C) and in the adjacent P+1 loop (M1250T). Additional weaker mutations have been found near the catalytic loop and within the A lobe of the kinase domain. Furthermore, some mutations in the juxtamembrane domain of c-Met have been observed in lung tumours which do not directly activate the kinase, but rather stabilize the protein by rendering it resistant to ubiquitination and subsequent degradation [M. Kong-Beltran et al., *Cancer Res.* 66: 283-9 (2006); T. E. Taher et al., *J. Immunol.* 169: 3793-800 (2002); P. Peschard et al., *Mol. Cell.* 8: 995-1004 (2001)]. Interestingly, somatic mutations of c-Met are associated with increased aggressiveness and extensive metastases in various cancers. While the frequency of germ line and somatic mutations is low (below 5%), other major mechanisms have been observed leading to a deregulation of the c-Met signalling, in the absence of mutations, by paracrine or autocrine mechanisms. Paracrine activation has been observed in tumours which are derived from mesenchymal cells, like osteosarcomas or rhabdomyosarcomas, which physiologically produce HGF, and in glioblastomas and mamma carcinomas which are of ectodermal origin.

However, the most frequent cases are carcinomas where c-Met is overexpressed as observed in carcinomas of the colon, pancreas, stomach, breast, prostate, ovary and liver. Overexpression may arise, for example, by gene amplification as observed in gastric and lung tumour cell lines. Very recently, overexpression of c-Met was detected in lung tumour cell lines which acquired resistance to EGF receptor inhibition [J. A. Engelmann et al., *Science* 316: 1039-1043 (2007)]. Some epithelial tumours that overexpress c-Met also co-express HGF, resulting in an autocrine c-Met/HGF stimulatory loop and thereby circumventing the need for stromal cell-derived HGF.

In general, it has been found that aberrant activation of c-Met in human cancer is typically associated with a poor prognosis, regardless of the specific mechanism [J. G. Christensen et al., *Cancer Lett.* 225: 1-26 (2005)].

In summary, a great number of in vitro and in vivo studies have been performed that validate c-Met as an important cancer target, and a comprehensive list can be viewed at http://www.vai.org/met [C. Birchmeier et al., *Nat. Rev. Mol. Cell. Biol.* 4: 915-25 (2003)]. Several strategies have been followed to attenuate aberrant Met signalling in human tumours including HGF antagonists and small molecule inhibitors, amongst others. A number of small molecule inhibitors are currently in clinical development, such as ARQ-197 (Arqule), foretinib (XL-880, Exelixis/GSK), and PH-2341066 (Pfizer); they have recently been reviewed [J. J. Cui, *Expert Opin. Ther. Patents* 17: 1035-45 (2007)].

The technical problem to be solved according to the present invention may therefore be seen in providing alternative compounds with potent inhibitory activity on the c-Met kinase, thus offering new therapeutic options for the treatment of c-Met-mediated diseases, particularly cancer and other proliferative disorders.

1,4-Dihydropyridine derivatives bearing a bicyclic heteroaryl group in 4-position that are useful as cardiovascular agents with calcium agonistic or antagonistic activity are known from EP 0 217 530-A1 and EP 0 630 895-A1. 3-Cyano-4-(hetero)aryl-1,4-dihydropyridines as modulators both of steroidal receptors and calcium channel activities being valuable for the treatment of cardiovascular diseases have been described in WO 2006/066011-A2. Recently, certain 3-cyano-4-heteroaryl-1,4-dihydropyridines possessing c-Met kinase inhibitory activity have been disclosed in WO 2008/071451-A1.

In one aspect, the present invention relates to 4-(furo[3,2-c]pyridin-2-yl)-1,4-dihydropyridine derivatives of the general formula (I)

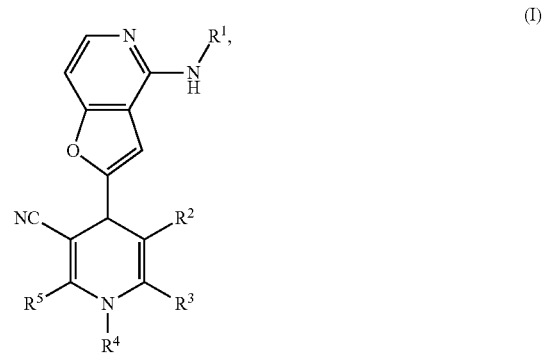

(I)

wherein
$R^1$ is hydrogen, $(C_1$-$C_6)$-alkyl, $(C_1$-$C_6)$-alkylcarbonyl, benzyl or benzoyl,
  wherein the phenyl part of said benzyl and benzoyl groups, respectively, may be substituted with one or two residues independently selected from the group consisting of fluoro, chloro, bromo, cyano, methyl, difluoromethyl, trifluoromethyl, ethyl, methoxy, difluoromethoxy and trifluoromethoxy,
$R^2$ is cyano,
$R^3$ is $(C_1$-$C_4)$-alkyl optionally substituted with up to three fluoro atoms,
or
$R^2$ and $R^3$ are joined and, taken together with the carbon atoms to which they are attached, form a fused ring of the formula

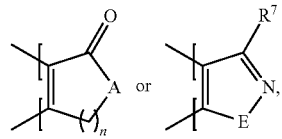

wherein
n is an integer of 1 or 2,
A is —$CH_2$—, —O— or —$NR^6$—, wherein
  $R^6$ is hydrogen or $(C_1$-$C_4)$-alkyl,
E is —O—, —NH— or —$NCH_3$—,
and
$R^7$ is hydrogen or methyl,
$R^4$ is hydrogen, $(C_1$-$C_4)$-alkyl or cyclopropyl, $R^5$ is $(C_1-C_6)$-alkyl optionally substituted with up to three fluoro atoms, or is phenyl or pyridyl each of which may be substituted with one or two residues independently selected from the group consisting of fluoro, chloro, bromo, cyano, methyl, difluoromethyl, trifluoromethyl, ethyl, methoxy, difluoromethoxy and trifluoromethoxy, or $R^4$ and $R^5$ are joined and, taken together with the nitrogen and the carbon atom to which they are attached, form a fused ring of the formula

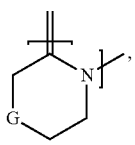

wherein

G is —$CH_2$— or —O—.

The compounds according to this invention can also be present in the form of their salts, hydrates and/or solvates.

Salts for the purposes of the present invention are preferably pharmaceutically acceptable salts of the compounds according to the invention (for example, see S. M. Berge et al., "Pharmaceutical Salts", J. Pharm. Sci. 1977, 66, 1-19).

Pharmaceutically acceptable salts include acid addition salts of mineral acids, carboxylic acids and sulfonic acids, for example salts of hydrochloric acid, hydrobromic acid, sulfuric acid, phosphoric acid, methanesulfonic acid, ethanesulfonic acid, benzenesulfonic acid, toluenesulfonic acid, naphthalenedisulfonic acid, acetic acid, propionic acid, lactic acid, tartaric acid, malic acid, citric acid, fumaric acid, maleic acid and benzoic acid.

Pharmaceutically acceptable salts also include salts of customary bases, such as for example and preferably alkali metal salts (for example, sodium and potassium salts), alkaline earth metal salts (for example, calcium and magnesium salts), and ammonium salts derived from ammonia or organic amines, such as illustratively and preferably ethylamine, diethylamine, triethylamine, N,N-diisopropylethylamine, monoethanolamine, diethanolamine, triethanolamine, dimethylaminoethanol, choline, ethylenediamine, dicyclohexylamine, dibenzylamine, N-methylmorpholine, N-methyl-piperidine, dihydroabietylamine, arginine and lysine.

Hydrates of the compounds of the invention or their salts are stoichiometric compositions of the compounds or salts with water, such as, for example, hemi-, mono- or dihydrates.

Solvates of the compounds of the invention or their salts are stoichiometric compositions of the compounds or salts with solvents.

The compounds of this invention may, either by nature of asymmetric centers or by restricted rotation, be present in the form of isomers (enantiomers, diastereomers). Any isomer may be present in which the asymmetric center is in the (R)—, (S)—, or (R,S)-configuration.

It will also be appreciated that when two or more asymmetric centers are present in the compounds of the invention, several diastereomers and enantiomers of the exemplified structures will often be possible, and that pure diastereomers and pure enantiomers represent preferred embodiments.

All isomers, whether separated, pure, partially pure, or in diastereomeric or racemic mixture, of the compounds of this invention are encompassed within the scope of this invention.

The purification of said isomers and the separation of said isomeric mixtures may be accomplished by standard techniques known in the art. For example, diastereomeric mixtures can be separated into the individual isomers by chromatographic processes or crystallization, and racemates can be separated into the respective enantiomers either by chromatographic processes on chiral phases or by resolution.

In addition, all possible tautomeric forms of the compounds described above are included according to the present invention.

Unless otherwise stated, the following definitions apply for the substituents and residues used throughout this specification and claims:

$(C_1-C_6)$-alkyl, $(C_1-C_5)$-alkyl and $(C_1-C_4)$-alkyl represent a straight-chain or branched saturated hydrocarbon radical having 1 to 6, 1 to 5 and 1 to 4 carbon atoms, respectively. A straight-chain or branched alkyl radical having 1 to 4 carbon atoms is preferred. Non-limiting examples include methyl, ethyl, n-propyl, iso-propyl, n-butyl, iso-butyl, sec-butyl, tert-butyl, 1-ethylpropyl, n-pentyl, iso-pentyl, neo-pentyl, n-hexyl and iso-hexyl. The same applies to radicals such as alkylcarbonyl and the like.

$(C_1-C_6)$-alkylcarbonyl represents a straight-chain or branched alkyl radical having 1 to 6 carbon atoms which is bonded to the rest of the molecule via a carbonyl group [—C(=O)-]. Non-limiting examples include acetyl, n-propionyl, n-butyryl, iso-butyryl, n-pentanoyl, pivaloyl, n-hexanoyl and n-heptanoyl.

Throughout this document, for the sake of simplicity, the use of singular language is given preference over plural language, but is generally meant to include the plural language if not otherwise stated. E.g., the expression "A method of treating a disease in a patient, comprising administering to a patient an effective amount of a compound of formula (I)" is meant to include the simultaneous treatment of more than one disease as well as the administration of more than one compound of formula (I).

In a preferred embodiment, the present invention relates to compounds of general formula (I), wherein $R^1$ is hydrogen, methyl, acetyl or benzoyl, $R^2$ is cyano, $R^3$ is methyl, difluoromethyl or trifluoromethyl, or $R^2$ and $R^3$ are joined and, taken together with the carbon atoms to which they are attached, form a fused ring of the formula

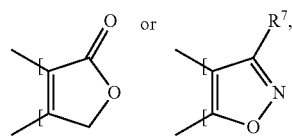

wherein $R^7$ is hydrogen or methyl, $R^4$ is hydrogen or methyl, $R^5$ is $(C_1-C_4)$-alkyl optionally substituted with up to three fluoro atoms, or is phenyl optionally substituted with one or two residues independently selected from the group consisting of fluoro, chloro, methyl and trifluoromethyl, or R⁴ and R⁵ are joined and, taken together with the nitrogen and the carbon atom to which they are attached, form a fused morpholine ring of the formula

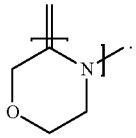

In a particularly preferred embodiment, the present invention relates to compounds of general formula (I), wherein R¹ is hydrogen or benzoyl, R² is cyano, R³ is methyl, difluoromethyl or trifluoromethyl, or R² and R³ are joined and, taken together with the carbon atoms to which they are attached, form a fused lactone ring of the formula

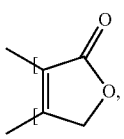

R⁴ is hydrogen, and

R⁵ is methyl, difluoromethyl or trifluoromethyl, or is phenyl optionally substituted with fluoro or chloro.

The definitions of residues indicated specifically in the respective combinations or preferred combinations of residues are also replaced as desired by definitions of residues of other combinations, irrespective of the particular combinations indicated for the residues. Combinations of two or more of the abovementioned preferred ranges are particularly preferred.

In another embodiment, the present invention relates to a process for preparing compounds of general formula (I), wherein R⁴ is hydrogen and R¹ represents hydrogen, (C₁-C₆)-alkylcarbonyl or optionally substituted benzoyl, characterized in that a furopyridinyl aldehyde of formula (II)

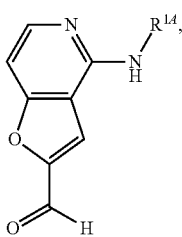

wherein

R¹⁴ represents (C₁-C₆)-alkylcarbonyl or optionally substituted benzoyl as defined above for R¹, is reacted either

[A] with a cyanoketone of formula (III)

or a sodium enolate thereof, wherein R⁵ has the meaning defined above, in the presence of an acid, acid/base combination and/or dehydrating agent to give a compound of formula (IV)

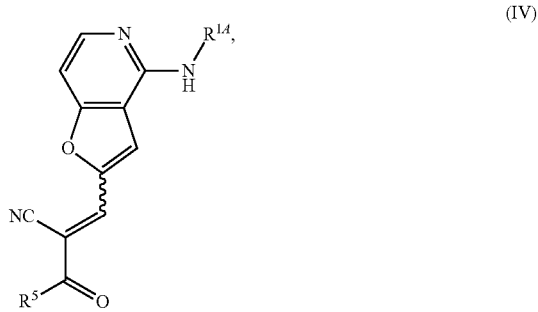

wherein R¹⁴ and R⁵ have the meanings defined above, and the latter is then condensed either with an enamine of formula (V)

wherein R² and R³ have the meanings defined above, or with a ketone of formula (VI)

wherein R² and R³ have the meanings defined above, in combination with an ammonia source, such as ammonium acetate, to yield the compound of formula (I-A)

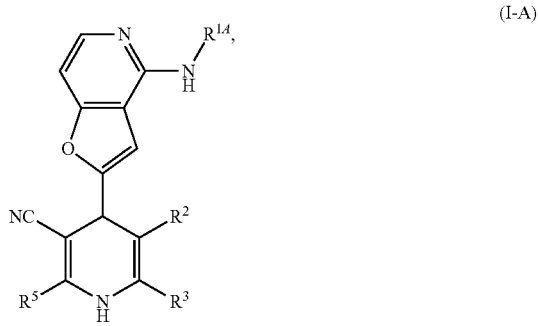

wherein $R^{14}$, $R^2$, $R^3$ and $R^5$ have the meanings defined above, or

[B] with a ketone of formula (VI)

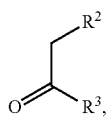
(VI)

wherein $R^2$ and $R^3$ have the meanings defined above, in the optional presence of an acid, base and/or dehydrating agent to give a compound of formula (VII)

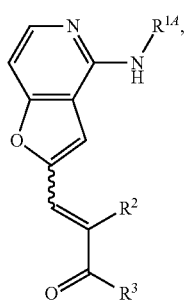
(VII)

wherein $R^{14}$, $R^2$ and $R^3$ have the meanings defined above, and the latter is then condensed with an enaminonitrile of formula (VIII)

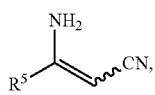
(VIII)

wherein $R^5$ has the meaning defined above, in the optional presence of an acid to also yield the compound of formula (I-A)

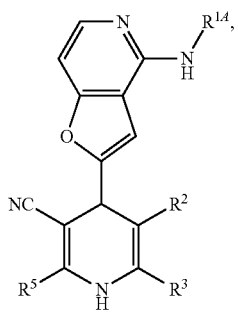
(I-A)

wherein $R^{14}$, $R^2$, $R^3$ and $R^5$ have the meanings defined above, optionally followed by hydrolytic cleavage of the acyl group $R^{14}$ to give the amine compound (I-B)

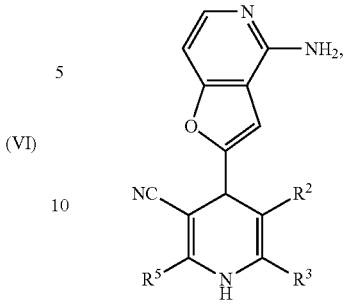
(I-B)

wherein $R^2$, $R^3$ and $R^5$ have the meanings defined above, and optionally followed, where appropriate, by (i) separating the compounds (I-A) and (I-B) thus obtained into their respective enantiomers and/or diastereomers, preferably using chromatographic methods, and/or (ii) converting the compounds (I-A) and (I-B) into their respective hydrates, solvates, salts and/or hydrates or solvates of the salts by treatment with the corresponding solvents and/or acids or bases.

The process variants [A] (II)+(III)→(IV), (IV)+(V)/(VI)→(I-A) and [B] (II)+(VI)→(VII), (VII)+(VIII)→(I-A) may both be carried out in two separate steps as described above, or by using a one-pot procedure, i.e. without explicit isolation of the respective intermediate compounds (IV) and (VII). In some cases, depending on the reactivity of individual reactants, it may also be feasible for preparing the compounds of formula (I-A) to perform a one-flask/three-component condensation reaction of compounds (II), (III) and (V)/(VI) [A], or (II), (VI) and (VIII) [B] [for the synthesis of 1,4-dihydropyridines in general, see, for example, D. M. Stout, A. I. Meyers, *Chem. Rev.* 1982, 82, 223-243; H. Meier et al., *Liebigs Ann. Chem.* 1977, 1888; H. Meier et al., *ibid.* 1977, 1895; H. Meier et al., *ibid.* 1976, 1762; F. Bossert et al., *Angew. Chem.* 1981, 93, 755].

Suitable ammonia sources for reaction (IV)+(VI)→(I-A) are, for example, ammonium formate, ammonium acetate, ammonium chloride or ammonium hydrogensulfate; preference is given to ammonium acetate.

Process steps (II)+(III)→(IV), (IV)+(V)/(VI)→(I-A), (II)+(VI)→(VII) and (VII)+(VIII)→(I-A) are generally carried out in an inert solvent at a temperature ranging from +20° C. to the boiling point of the solvent under atmospheric pressure.

Solvents suitable for this purpose are, for example, alcohols such as methanol, ethanol, n-propanol, isopropanol, n-butanol, tert-butanol or n-pentanol, hydrocarbons such as hexane, cyclohexane, benzene, toluene or xylene, halohydrocarbons such as dichloromethane, trichloromethane, tetrachloromethane, trichloroethane, 1,2-dichloroethane, chlorobenzene or chlorotoluene, ethers such as tetrahydrofuran, 1,4-dioxane or 1,2-dimethoxyethane, or other solvents such as acetonitrile or acetic acid. It is likewise possible to use mixtures of these solvents. Reactions (II)+(III)→(IV) and (II)+(VI)→(VII) are preferably performed in dichloromethane, toluene, ethanol, n-propanol, isopropanol, n-butanol or n-pentanol at the respective reflux temperature under atmospheric pressure, and reactions (IV)+(V)/(VI)→(I-A) and (VII)+(VIII)→(I-A) are preferably carried out in n-propanol, isopropanol, n-butanol, n-pentanol, xylene, acetic acid or mixtures thereof also at reflux temperature under atmospheric pressure.

Reaction (II)+(III)→(IV) may advantageously take place in the presence of an acid, an acid/base combination and/or an inert dehydrating agent such as, for example, molecular sieves. Examples of suitable acid catalysts are acetic acid, trifluoroacetic acid, methanesulfonic acid, benzenesulfonic acid or p-toluenesulfonic acid; suitable bases are in particular piperidine or pyridine. Depending on the reactivity of the components, conversion (II)+(VI)→(VII) may be performed without further auxiliary reagents, or it can be facilitated by a customary amine base, such as, for example, piperidine, by an acid, such as acetic acid, and/or by a dehydrating agent, such as molecular sieves. Similarly, reactions (IV)+(V)/(VI)→(I-A) and (VII)+(VIII)→(I-A) may be carried out without further catalysis or with the aid of an acid additive; in the latter case, acetic acid is preferably used both as acid catalyst and solvent or co-solvent.

In case $R^{1A}$ is an optionally substituted benzoyl group, the cleavage reaction (I-A)→(I-B) is preferably carried out by exposing the compound (I-A) at elevated temperature (e.g. from +50° C. to +120° C.) to a strong acid, such as hydrogen chloride or hydrogen bromide, in glacial acetic acid solution. In case $R^{1A}$ is a $(C_1-C_6)$-alkylcarbonyl group, hydrolysis is usually performed under basic conditions by treating the compound (I-A) with aqueous alkali hydroxide, such as lithium, sodium or potassium hydroxide, in a protic or water-miscible solvent, such as methanol, ethanol, isopropanol, tetrahydrofuran, 1,4-dioxane or 1,2-dimethoxyethane, at a temperature range from 0° C. to +60° C.

Compounds of formula (I-A), wherein $R^2$ is cyano and $R^3$ and $R^5$ both represent optionally fluoro-substituted $(C_1-C_4)$-alkyl residues that are identical to each other [i.e. compounds of formula (I-A) having a symmetrical 1,4-dihydropyridine substructure], may alternatively be prepared by condensing the furopyridinyl aldehyde of formula (II)

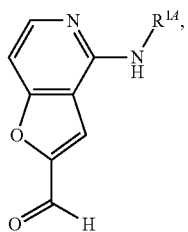

(II)

wherein $R^{1A}$ has the meaning defined above,
in the presence of an acid with two equivalents of the cyanoenamine of formula (V-A)

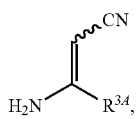

(V-A)

wherein
$R^{3A}$ represents $(C_1-C_4)$-alkyl optionally substituted with up to three fluoro atoms, to yield the compound of formula (I-A1)

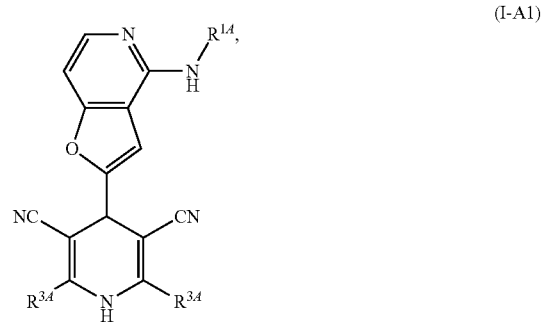

(I-A1)

wherein $R^{1A}$ and $R^{3A}$ have the meanings defined above.

The condensation reaction (II)+(V-A)→(I-A1) is usually performed in protic organic solvents like alcohols, such as methanol, ethanol, n-propanol, isopropanol, n-butanol, tert-butanol or n-pentanol, or acetic acid. It is likewise possible to use mixtures of these solvents. Examples of acid catalysts benefiting this conversion are acetic acid, trifluoroacetic acid, methanesulfonic acid, benzenesulfonic acid and p-toluenesulfonic acid. Preferably, acetic acid is simultaneously used as acid catalyst and solvent or co-solvent.

Process step (II)+(V-A)→(1-A1) is generally carried out at a temperature range from +20° C. to +150° C., preferably from +80° C. to +125° C., under atmospheric pressure.

Compounds of the invention having the formula (I-A2)

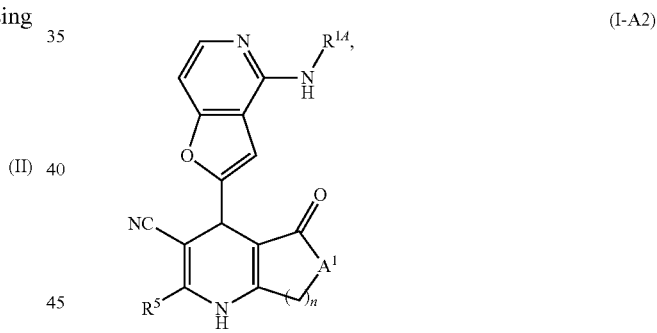

(I-A2)

wherein $R^{1A}$, $R^5$ and n have the meanings defined above, and
$A^1$ represents —O— or —$NR^6$—, wherein $R^6$ has the meaning defined above,
may also be prepared by a three-component condensation reaction of the furopyridinyl aldehyde (II)

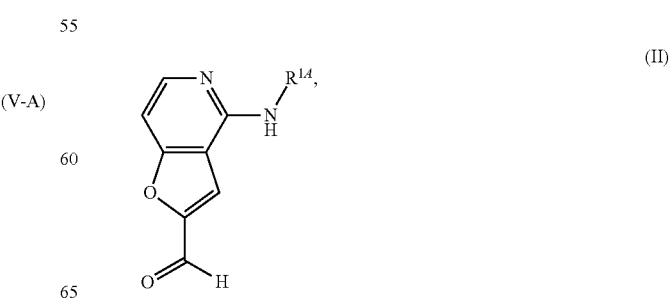

(II)

wherein $R^{1A}$ has the meaning defined above, with the enaminonitrile of formula (VIII)

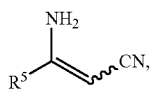
(VIII)

wherein $R^5$ has the meaning defined above,
and a ketoester of formula (IX)

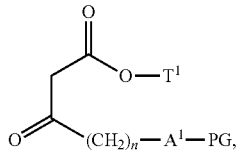
(IX)

wherein n and $A^1$ have the meanings defined above,
$T^1$ represents $(C_1-C_4)$-alkyl,
and
PG represents a suitable hydroxy- or amino-protecting group, such as acetyl, trimethylsilyl, tetrahydropyranyl, tert-butoxycarbonyl or benzyloxycarbonyl, respectively,
to give an intermediate compound of formula (X)

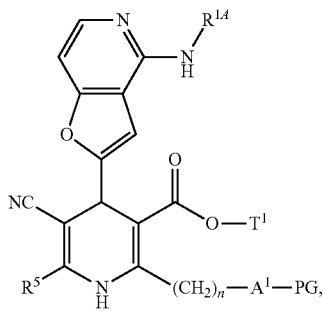
(X)

wherein $R^{14}$, $R^5$, n, $A^1$, $T^1$ and PG have the meanings defined above,
which is then deprotected and cyclized to yield the target compound of formula (I-A2).

The condensation reaction (II)+(VIII)+(IX)→(X) is preferably carried out in an alcoholic solvent such as methanol, ethanol, n-propanol, isopropanol, n-butanol, tert-butanol or n-pentanol, optionally in combination with an acid catalyst such as acetic acid. The conversion is generally performed at a temperature range from +20° C. to +150° C., preferably from +80° C. to +125° C., under atmospheric pressure.

The removal of the protecting group PG in process step (X)→(I-A2) is generally accomplished by standard methods well known in the art [see, for example, T. W. Greene and P. G. M. Wuts, *Protective Groups in Organic Synthesis*, Wiley, New York, 1999]. As a hydroxy-protecting group, acetyl is preferably used. In this case, deprotection and subsequent lactone formation [$A^1$=O in (I-A2)] may be performed in a one-pot procedure, i.e. without isolation of the deprotected intermediate, by treating the compound (X) with an aqueous solution of a strong acid, such as hydrogen chloride, hydrogen bromide or trifluoroacetic acid, at elevated temperature (e.g. from +50° C. to +120° C.).

For nitrogen protection, tert-butoxycarbonyl (Boc) is preferably employed as group PG. Deprotection by standard treatment with anhydrous hydrogen chloride or trifluoroacetic acid, and final cyclization to lactame (I-A2) [$A^1$=$NR^6$] by exposing the intermediate amine salt to a customary base may again be performed using a one-pot procedure or in two separate steps.

Compounds of the invention having the formula (I—C)

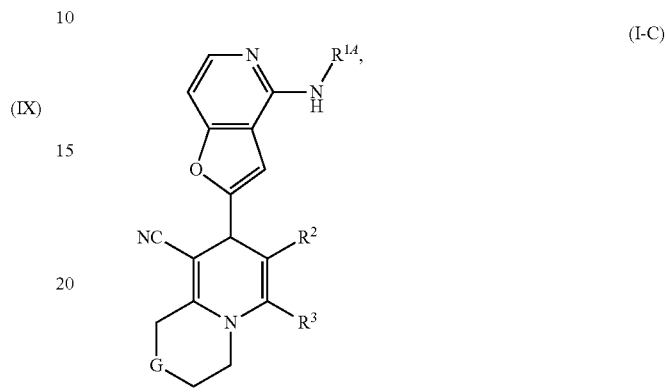
(I-C)

wherein $R^{14}$, $R^2$, $R^3$ and G have the meanings defined above, can be prepared in close analogy to the condensation reactions described above by substituting the compound of formula (XI)

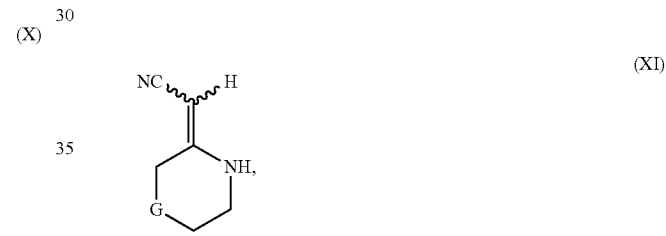
(XI)

wherein G has the meaning defined above,
for the enaminonitrile of formula (VIII) [cf. transformations (VII)+(VIII)→(I-A) and (II)+(VIII)+(IX)→(X)→(I-A2), respectively]. The reaction parameters specified above, such as solvents and acid catalysts, are applied analogously.

Compound (I-C) may then be converted, if desired, into the corresponding 4-aminofuropyridinyl derivative of formula (I-D)

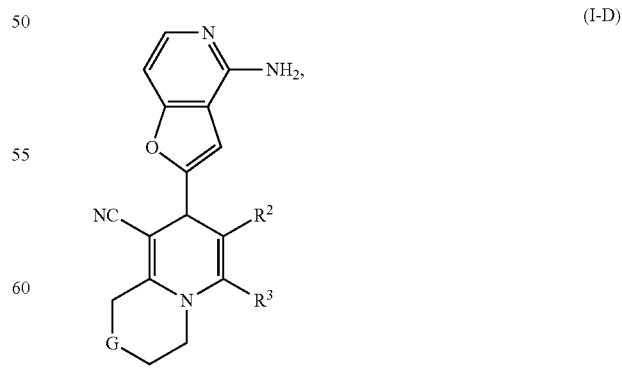
(I-D)

wherein $R^2$, $R^3$ and G have the meanings defined above,
by hydrolytic removal of the acyl group $R^{14}$ [cf. transformation (I-A)→(I-B)].

The exocyclic enamine of formula (XI) may be prepared starting from a lactam of formula (XII)

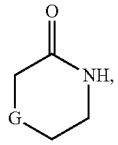
(XII)

wherein G has the meaning defined above,
which is first condensed via its lactim ether derivative of formula (XIII)

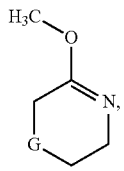
(XIII)

wherein G has the meaning defined above,
with a cyanoacetate of formula (XIV)

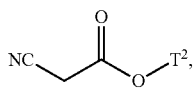
(XIV)

wherein
$T^2$ represents $(C_1$-$C_4)$-alkyl or benzyl,
to give a compound of formula (XV)

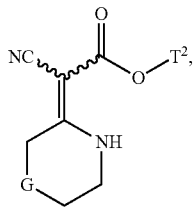
(XV)

wherein G and $T^2$ have the meanings defined above,
which upon ester cleavage and decarboxylation yields the cyano-enamine of formula (XI) [see reaction scheme 5 below]. This intermediate is usually employed in the subsequent reactions as a solution of the crude material, i.e. without further isolation and purification.

Compounds of formula (I), wherein $R^4$ is $(C_1$-$C_4)$-alkyl or cyclopropyl, can be prepared by reacting the compound of formula (I-A) in the presence of a base with a compound of formula (XVI)

$R^{4A}$—Z (XVI), wherein
$R^{4A}$ represents $(C_1$-$C_4)$-alkyl or cyclopropyl,
and Z represents a leaving group, such as halogen, mesylate, triflate, tosylate or sulfate, to yield the compound of formula (I-E)

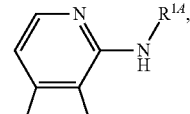
(I-E)

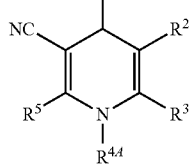

wherein $R^{1A}$, $R^2$, $R^3$, $R^{4A}$ and $R^5$ have the meanings defined above,
which may then be hydrolyzed, if desired, to give the 4-aminofuropyridinyl derivative of formula (I-F)

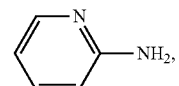
(I-F)

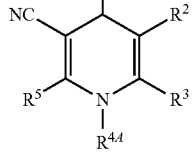

wherein $R^2$, $R^3$, $R^{4A}$ and $R^5$ have the meanings defined above [cf. transformation (I-A)→(LB)].

Inert solvents for the alkylation reaction (I-A)+(XVI)→(1-E) are, for example, ethers such as diethyl ether, methyl tert-butyl ether, tetrahydrofuran, 1,4-dioxane or 1,2-dimethoxyethane, hydrocarbons such as benzene, toluene, xylene, hexane or cyclohexane, halohydrocarbons such as dichloromethane, trichloromethane, tetrachloromethane, 1,2-dichloroethane, trichloroethane, tetrachloroethane, chlorobenzene or chlorotoluene, or other solvents such as acetonitrile, N,N-dimethylformamide (DMF), dimethylsulfoxide (DMSO), N,N'-dimethylpropylene urea (DMPU), N-methylpyrrolidinone (NMP) or pyridine. It is also feasible to use mixtures of these solvents. Preferably, dichloromethane, tetrahydrofuran, N,N-dimethylformamide or mixtures thereof are employed.

Bases suitable for process step (I-A)+(XVI)→(I-E) are in particular alkali metal or alkaline earth metal carbonates such as lithium, sodium, potassium, calcium or caesium carbonate, alkali metal hydrides such as sodium or potassium hydride, sterically hindered alkali alkoxides such as sodium or potassium tert-butoxide, sterically hindered alkali amides such as lithium, sodium or potassium bis(trimethylsilyl)amide or lithium diisopropylamide, or organic amines such as triethylamine, N-methylmorpholine, N-methylpiperidine, N,N-diisopropylethylamine or pyridine. Potassium carbonate, caesium carbonate, sodium hydride or triethylamine are preferably used.

Reaction (I-A)+(XVI)→(I-E) is generally performed under atmospheric pressure at a temperature range from −20° C. to +100° C., preferably at 0° C. to +50° C.

Compounds of formula (I), wherein $R^1$ is $(C_1-C_6)$-alkyl or optionally substituted benzyl, may be prepared by reacting a compound of formula (I-B), (I-D) or (I-F), respectively, with an aldehyde of formula (XVII)

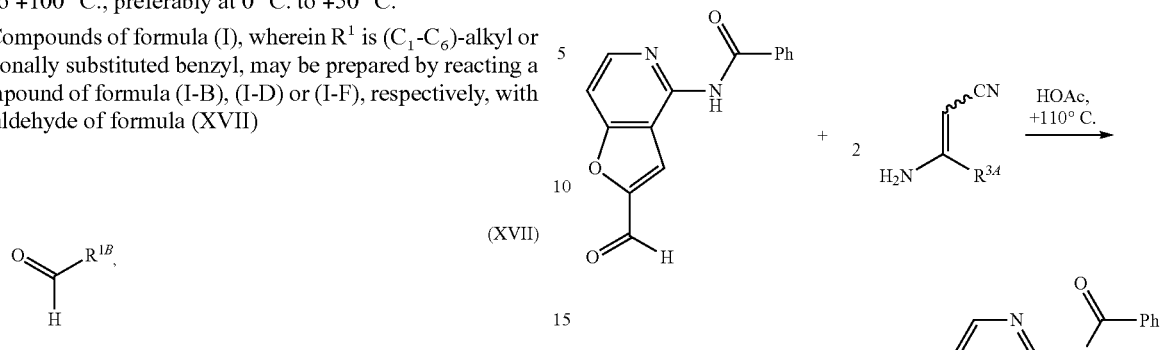

(XVII)

wherein $R^{1B}$ represents hydrogen, $(C_1-C_5)$-alkyl or optionally substituted phenyl as defined above for $R^1$, in the presence of a suitable reducing agent, such as sodium borohydride, to give the compound of formula (I-G)

(I-G)

wherein $R^{1B}$, $R^2$, $R^3$, $R^4$ and $R^5$ have the meanings defined above.

The transformation is usually carried out in a protic solvent, such as water, methanol, ethanol, isopropanol or mixtures thereof, at a temperature range from 0° C. to +50° C. under atmospheric pressure. Reducing agents commonly employed in this type of N-alkylation reaction are alkali borohydride derivatives, such as sodium borohydride, potassium borohydride, sodium cyanoborohydride or sodium triacetoxyborohydride, optionally in combination with an acid catalyst such as acetic acid.

The compounds of the formulae (II), (III), (V), (V-A), (VI), (VIII), (IX), (XII), (XIV), (XVI) and (XVII) are either commercially available, known from the literature, or can be prepared from readily available starting materials by adaptation of standard methods described in the literature (for further references, see experimental section below).

The preparation of the compounds of the invention can be illustrated by means of the following synthesis schemes 1-5. More detailed procedures are presented below in the experimental section describing the Examples.

Scheme 1

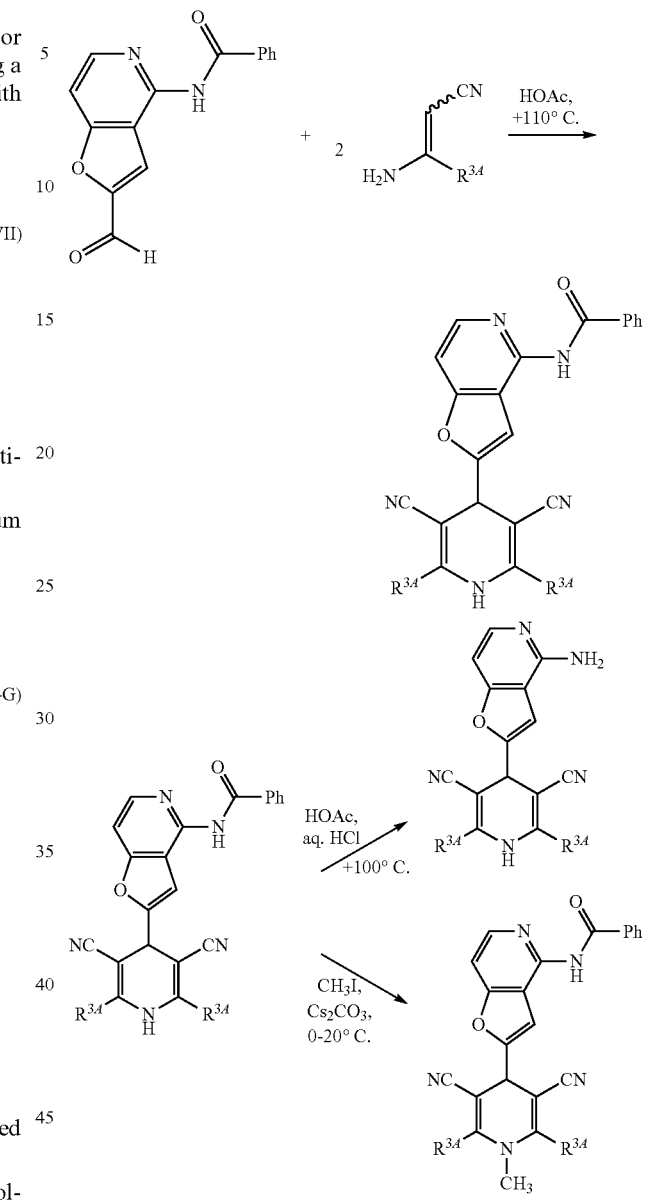

Scheme 2

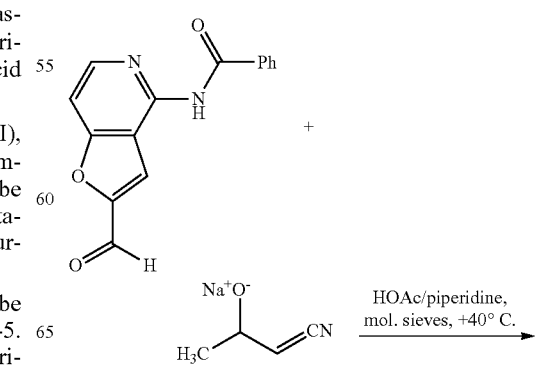

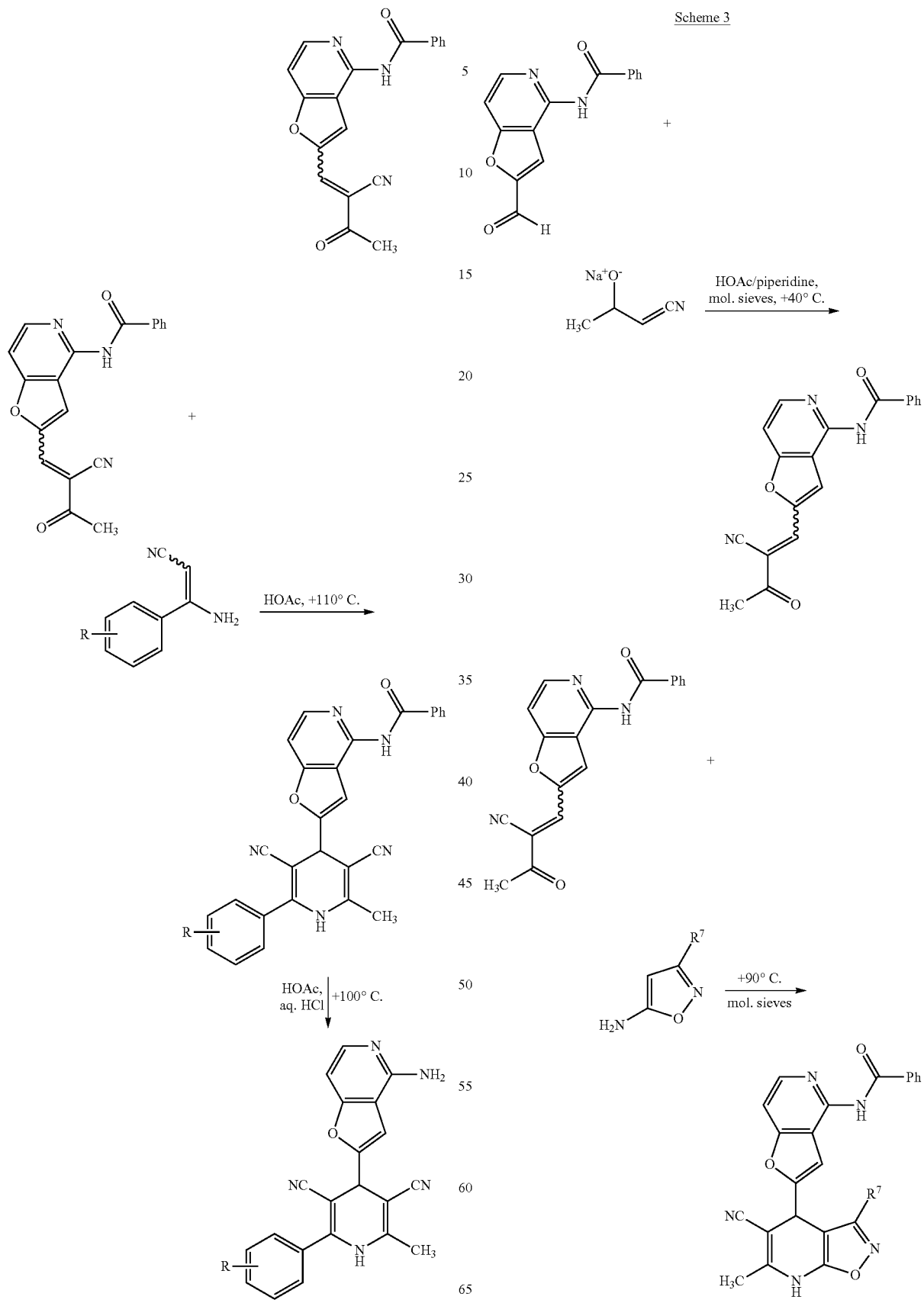

Scheme 4

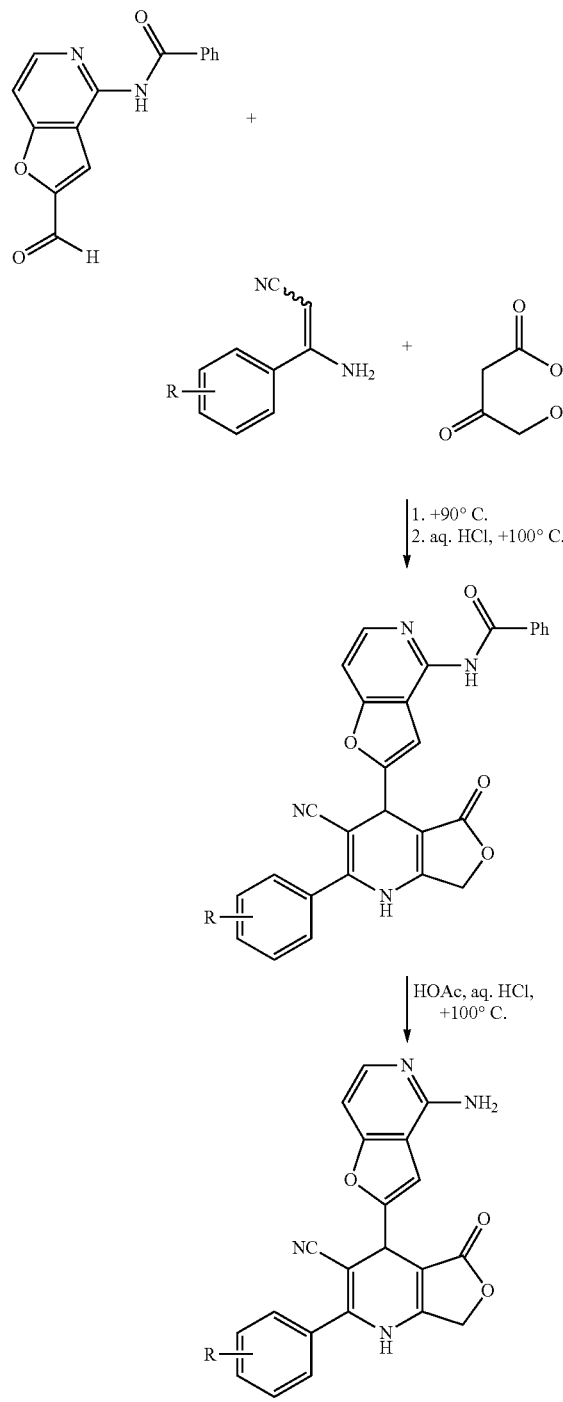

Scheme 5

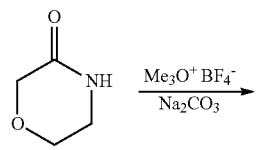

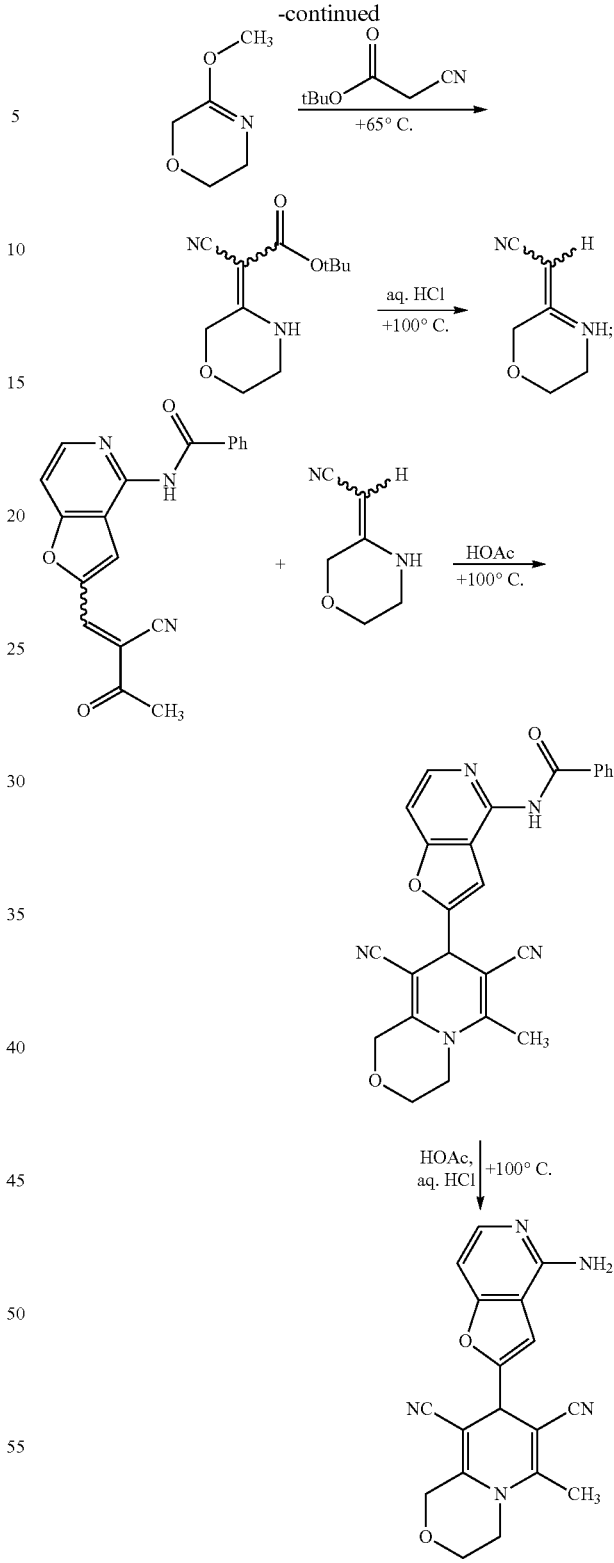

Methods of Use

The compounds of the present invention may be used to inhibit the activity or expression of receptor tyrosine kinases, particularly of the c-Met receptor tyrosine kinase. Therefore, the compounds of formula (I) are expected to be valuable as therapeutic agents. Accordingly, in another embodiment, the present invention provides a method of treating disorders relating to or mediated by c-Met kinase activity in a patient in need of such treatment, comprising administering to the patient an effective amount of a compound of formula (I) as defined above. In certain embodiments, the disorders relating to c-Met kinase activity are cell proliferative disorders, particularly cancer.

The term "treating" or "treatment" as stated throughout this document is used conventionally, e.g., the management or care of a subject for the purpose of combating, alleviating, reducing, relieving, improving the condition of a disease or disorder, such as a carcinoma.

The term "subject" or "patient" includes organisms which are capable of suffering from a cell proliferative disorder or who could otherwise benefit from the administration of a compound of the invention, such as human and non-human animals. Preferred humans include human patients suffering from or prone to suffering from a cell proliferative disorder or associated state, as described herein. The term "non-human animals" includes vertebrates, e.g., mammals, such as non-human primates, sheep, cow, dog, cat and rodents, e.g., mice, and non-mammals, such as chickens, amphibians, reptiles, etc.

The term "disorders relating to or mediated by c-Met" shall include diseases associated with or implicating c-Met activity, for example the hyperactivity of c-Met, and conditions that accompany with these diseases. Examples of "disorders relating to or mediated by c-Met" include disorders resulting from overstimulation of c-Met due to abnormally high amount of c-Met or mutations in c-Met, or disorders resulting from abnormally high amount of c-Met activity due to abnormally high amount of c-Met or mutations in c-Met.

The term "hyperactivity of c-Met" refers to either c-Met expression in cells which normally do not express c-Met or c-Met activity by cells which normally do not possess active c-Met or increased c-Met expression leading to unwanted cell proliferation or mutations leading to constitutive activation of c-Met.

The term "cell proliferative disorder" includes disorders involving the undesired or uncontrolled proliferation of a cell. The compounds of the present invention can be utilized to prevent, inhibit, block, reduce, decrease, control, etc., cell proliferation and/or cell division, and/or produce apoptosis. This method comprises administering to a subject in need thereof, including a mammal, including a human, an amount of a compound of this invention, or a pharmaceutically acceptable salt, isomer, polymorph, metabolite, hydrate or solvate thereof which is effective to treat or prevent the disorder.

Cell proliferative or hyper-proliferative disorders in the context of this invention include, but are not limited to, e.g., psoriasis, keloids and other hyperplasias affecting the skin, endometriosis, skeletal disorders, angiogenic or blood vessel proliferative disorders, pulmonary hypertension, fibrotic disorders, mesangial cell proliferative disorders, colonic polyps, polycystic kidney disease, benign prostate hyperplasia (BPH), and solid tumors, such as cancers of the breast, respiratory tract, brain, reproductive organs, digestive tract, urinary tract, eye, liver, skin, head and neck, thyroid, parathyroid, and their distant metastases. Those disorders also include lymphomas, sarcomas and leukemias.

Examples of breast cancer include, but are not limited to invasive ductal carcinoma, invasive lobular carcinoma, ductal carcinoma in situ, and lobular carcinoma in situ.

Examples of cancers of the respiratory tract include, but are not limited to small-cell and non-small-cell lung carcinoma, as well as bronchial adenoma and pleuropulmonary blastoma.

Examples of brain cancers include, but are not limited to brain stem and hypophtalmic glioma, cerebellar and cerebral astrocytoma, glioblastoma, medulloblastoma, ependymoma, as well as neuroectodermal and pineal tumor.

Tumors of the male reproductive organs include, but are not limited to prostate and testicular cancer. Tumors of the female reproductive organs include, but are not limited to endometrial, cervical, ovarian, vaginal and vulvar cancer, as well as sarcoma of the uterus.

Tumors of the digestive tract include, but are not limited to anal, colon, colorectal, esophageal, gallbladder, gastric, pancreatic, rectal, small-intestine, and salivary gland cancers.

Tumors of the urinary tract include, but are not limited to bladder, penile, kidney, renal pelvis, ureter, urethral, and hereditary and sporadic papillary renal cancers.

Eye cancers include, but are not limited to intraocular melanoma and retinoblastoma.

Examples of liver cancers include, but are not limited to hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to squamous cell carcinoma, Kaposi's sarcoma, malignant melanoma, Merkel cell skin cancer, and non-melanoma skin cancer.

Head-and-neck cancers include, but are not limited to laryngeal, hypopharyngeal, nasopharyngeal, oropharyngeal cancer, lip and oral cavity cancer, and squamous cell cancer.

Lymphomas include, but are not limited to AIDS-related lymphoma, non-Hodgkin's lymphoma, cutaneous T-cell lymphoma, Burkitt lymphoma, Hodgkin's disease, and lymphoma of the central nervous system.

Sarcomas include, but are not limited to sarcoma of the soft tissue, osteosarcoma, malignant fibrous histiocytoma, lymphosarcoma, and rhabdomyosarcoma.

Leukemias include, but are not limited to acute myeloid leukemia, acute lymphoblastic leukemia, chronic lymphocytic leukemia, chronic myelogenous leukemia, and hairy cell leukemia.

Fibrotic proliferative disorders, i.e. the abnormal formation of extracellular matrices, that may be treated with the compounds and methods of the present invention include lung fibrosis, atherosclerosis, restenosis, hepatic cirrhosis, and mesangial cell proliferative disorders, including renal diseases such as glomerulonephritis, diabetic nephropathy, malignant nephrosclerosis, thrombotic microangiopathy syndromes, transplant rejection, and glomerulopathies.

Other conditions in humans or other mammals that may be treated by administering a compound of the present invention include tumor growth, retinopathy, including diabetic retinopathy, ischemic retinal-vein occlusion, retinopathy of prematurity and age-related macular degeneration, rheumatoid arthritis, psoriasis, and bullous disorders associated with subepidermal blister formation, including bullous pemphigoid, erythema multiforme and dermatitis herpetiformis.

The compounds of the present invention may also be used to prevent and treat diseases of the airways and the lung, diseases of the gastrointestinal tract as well as diseases of the bladder and bile duct.

The disorders mentioned above have been well characterized in humans, but also exist with a similar etiology in other animals, including mammals, and can be treated by administering pharmaceutical compositions of the present invention.

Compounds of formula (I) may be administered as the sole pharmaceutical agent or in combination with one or more additional therapeutic agents where the combination causes no unacceptable adverse effects. This combination therapy includes administration of a single pharmaceutical dosage formulation which contains a compound of formula (I) and one or more additional therapeutic agents, as well as administration of the compound of formula (I) and each additional therapeutic agent in its own separate pharmaceutical dosage formulation. For example, a compound of formula (I) and a therapeutic agent may be administered to the patient together in a single oral dosage composition such as a tablet or capsule, or each agent may be administered in separate dosage formulations.

Where separate dosage formulations are used, the compound of formula (I) and one or more additional therapeutic agents may be administered at essentially the same time (e.g., concurrently) or at separately staggered times (e.g., sequentially).

In particular, the compounds of the present invention may be used in fixed or separate combination with other anti-tumor agents such as alkylating agents, anti-metabolites, plant-derived anti-tumor agents, hormonal therapy agents, topoisomerase inhibitors, camptothecin derivatives, kinase inhibitors, targeted drugs, antibodies, interferons and/or biological response modifiers, anti-angiogenic compounds, and other anti-tumor drugs. In this regard, the following is a non-limiting list of examples of secondary agents that may be used in combination with the compounds of the present invention:

Alkylating agents include, but are not limited to, nitrogen mustard N-oxide, cyclophosphamide, ifosfamide, thiotepa, ranimustine, nimustine, temozolomide, altretamine, apaziquone, brostallicin, bendamustine, carmustine, estramustine, fotemustine, glufosfamide, mafosfamide, bendamustin, and mitolactol; platinum-coordinated alkylating compounds include, but are not limited to, cisplatin, carboplatin, eptaplatin, lobaplatin, nedaplatin, oxaliplatin, and satraplatin;

Anti-metabolites include, but are not limited to, methotrexate, 6-mercaptopurine riboside, mercaptopurine, 5-fluorouracil alone or in combination with leucovorin, tegafur, doxifluridine, carmofur, cytarabine, cytarabine ocfosfate, enocitabine, gemcitabine, fludarabin, 5-azacitidine, capecitabine, cladribine, clofarabine, decitabine, eflornithine, ethynylcytidine, cytosine arabinoside, hydroxyurea, melphalan, nelarabine, nolatrexed, ocfosfite, disodium premetrexed, pentostatin, pelitrexol, raltitrexed, triapine, trimetrexate, vidarabine, vincristine, and vinorelbine;

Hormonal therapy agents include, but are not limited to, exemestane, Lupron, anastrozole, doxercalciferol, fadrozole, formestane, 11-beta hydroxysteroid dehydrogenase 1 inhibitors, 17-alpha hydroxylase/17,20 lyase inhibitors such as abiraterone acetate, 5-alpha reductase inhibitors such as finasteride and epristeride, anti-estrogens such as tamoxifen citrate and fulvestrant, Trelstar, toremifene, raloxifene, lasofoxifene, letrozole, anti-androgens such as bicalutamide, flutamide, mifepristone, nilutamide, Casodex, and anti-progesterones and combinations thereof;

Plant-derived anti-tumor substances include, e.g., those selected from mitotic inhibitors, for example epothilones such as sagopilone, ixabepilone and epothilone B, vinblastine, vinflunine, docetaxel, and paclitaxel;

Cytotoxic topoisomerase inhibiting agents include, but are not limited to, aclarubicin, doxorubicin, amonafide, belotecan, camptothecin, 10-hydroxycamptothecin, 9-aminocamptothecin, diflomotecan, irinotecan, topotecan, edotecarin, epimbicin, etoposide, exatecan, gimatecan, lurtotecan, mitoxantrone, pirambicin, pixantrone, rubitecan, sobuzoxane, tafluposide, and combinations thereof;

Immunologicals include interferons such as interferon alpha, interferon alpha-2a, interferon alpha-2b, interferon beta, interferon gamma-1a and interferon gamma-n1, and other immune enhancing agents such as L19-IL2 and other IL2 derivatives, filgrastim, lentinan, sizofilan, TheraCys, ubenimex, aldesleukin, alemtuzumab, BAM-002, dacarbazine, daclizumab, denileukin, gemtuzumab, ozogamicin, ibritumomab, imiquimod, lenograstim, lentinan, melanoma vaccine (Corixa), molgramostim, sargramostim, tasonermin, tecleukin, thymalasin, tositumomab, Vimlizin, epratuzumab, mitumomab, oregovomab, pemtumomab, and Provenge;

Biological response modifiers are agents that modify defense mechanisms of living organisms or biological responses such as survival, growth or differentiation of tissue cells to direct them to have anti-tumor activity; such agents include, e.g., krestin, lentinan, sizofuran, picibanil, ProMune, and ubenimex;

Anti-angiogenic compounds include, but are not limited to, acitretin, aflibercept, angiostatin, aplidine, asentar, axitinib, bevacizumab, brivanib alaninat, cilengtide, combretastatin, endostatin, fenretinide, halofuginone, pazopanib, ranibizumab, rebimastat, recentin, regorafenib, removab, revlimid, sorafenib, squalamine, sunitinib, telatinib, thalidomide, ukrain, vatalanib, and vitaxin;

Antibodies include, but are not limited to, trastuzumab, cetuximab, bevacizumab, rituximab, ticilimumab, ipilimumab, lumiliximab, catumaxomab, atacicept, oregovomab, and alemtuzumab;

VEGF inhibitors such as, e.g., sorafenib, regorafenib, bevacizumab, sunitinib, recentin, axitinib, aflibercept, telatinib, brivanib alaninate, vatalanib, pazopanib, and ranibizumab;

EGFR (HER1) inhibitors such as, e.g., cetuximab, panitumumab, vectibix, gefitinib, erlotinib, and Zactima;

HER2 inhibitors such as, e.g., lapatinib, tratuzumab, and pertuzumab;

mTOR inhibitors such as, e.g., temsirolimus, sirolimus/Rapamycin, and everolimus;

c-Met inhibitors;

PI3K and AKT inhibitors;

CDK inhibitors such as roscovitine and flavopiridol;

Spindle assembly checkpoints inhibitors and targeted anti-mitotic agents such as PLK inhibitors, Aurora inhibitors (e.g. Hesperadin), checkpoint kinase inhibitors, and KSP inhibitors;

HDAC inhibitors such as, e.g., panobinostat, vorinostat, MS275, belinostat, and LBH589;

HSP90 and HSP70 inhibitors;

Proteasome inhibitors such as bortezomib and carfilzomib;

Serine/threonine kinase inhibitors including MEK inhibitors and Raf inhibitors such as sorafenib;

Farnesyl transferase inhibitors such as, e.g., tipifarnib;

Tyrosine kinase inhibitors including, e.g., dasatinib, nilotibib, regorafenib, bosutinib, sorafenib, bevacizumab, sunitinib, cediranib, axitinib, aflibercept, telatinib, imatinib mesylate, brivanib alaninate, pazopanib, ranibizumab, vatalanib, cetuximab, panitumumab, vectibix, gefitinib, erlotinib, lapatinib, tratuzumab, pertuzumab, and c-Kit inhibitors;

Vitamin D receptor agonists;

Bcl-2 protein inhibitors such as obatoclax, oblimersen sodium, and gossypol;

Cluster of differentiation 20 receptor antagonists such as, e.g., rituximab;

Ribonucleotide reductase inhibitors such as, e.g., gemcitabine;

Tumor necrosis apoptosis inducing ligand receptor 1 agonists such as, e.g., mapatumumab;

5-Hydroxytryptamine receptor antagonists such as, e.g., rEV598, xaliprode, palonosetron hydrochloride, granisetron, Zindol, and AB-1001;

Integrin inhibitors including alpha5-beta1 integrin inhibitors such as, e.g., E7820, JSM 6425, volociximab, and endostatin;

Androgen receptor antagonists including, e.g., nandrolone decanoate, fluoxymesterone, Android, Prost-aid, andromustine, bicalutamide, flutamide, apo-cyproterone, apo-flutamide, chlormadinone acetate, Androcur, Tabi, cyproterone acetate, and nilutamide;

Aromatase inhibitors such as, e.g., anastrozole, letrozole, testolactone, exemestane, aminoglutethimide, and formestane;

Matrix metalloproteinase inhibitors;

Other anti-cancer agents including, e.g., alitretinoin, ampligen, atrasentan bexarotene, bortezomib, bosentan, calcitriol, exisulind, fotemustine, ibandronic acid, miltefosine, mitoxantrone, I-asparaginase, procarb azine, dacarb azine, hydroxycarbamide, pegaspargase, pentostatin, tazaroten, velcade, gallium nitrate, canfosfamide, darinaparsin, and tretinoin.

In a preferred embodiment, the compounds of the present invention may be used in combination with chemotherapy (i.e. cytotoxic agents), anti-hormones and/or targeted therapies such as other kinase inhibitors (for example, EGFR inhibitors), mTOR inhibitors and angiogenesis inhibitors.

The compounds of the present invention may also be employed in cancer treatment in conjunction with radiation therapy and/or surgical intervention.

Furthermore, the compounds of formula (I) may be utilized, as such or in compositions, in research and diagnostics, or as analytical reference standards, and the like, which are well known in the art.

Pharmaceutical Compositions and Methods of Treatment

In another aspect, the invention provides a pharmaceutical composition comprising a compound of formula (I) as defined above, together with a pharmaceutically acceptable carrier.

In still another aspect, the invention provides a process for preparing a pharmaceutical composition. The process includes the step of comprising combining at least one compound of formula (I) as defined above with at least one pharmaceutically acceptable carrier, and bringing the resulting combination into a suitable administration form.

The active component of formula (I) can act systemically and/or locally. For this purpose, it can be applied in a suitable manner, for example orally, parenterally, pulmonally, nasally, sublingually, lingually, buccally, rectally, transdermally, conjunctivally, otically, or as an implant or stent.

For these application routes, the active component of formula (I) can be administered in suitable application forms.

Useful oral application forms include application forms which release the active component rapidly and/or in modified form, such as, for example, tablets (non-coated and coated tablets, for example with an enteric coating), capsules, sugar-coated tablets, granules, pellets, powders, emulsions, suspensions, solutions and aerosols.

Parenteral application can be carried out with avoidance of an absorption step (intravenously, intraarterially, intracardially, intraspinally or intralumbarly) or with inclusion of an absorption (intramuscularly, subcutaneously, intracutaneously, percutaneously or intraperitoneally). Useful parenteral application forms include injection and infusion preparations in the form of solutions, suspensions, emulsions, lyophilisates and sterile powders.

Forms suitable for other application routes include, for example, inhalatory pharmaceutical forms (including powder inhalers, nebulizers), nasal drops, solutions or sprays, tablets or capsules to be administered lingually, sublingually or buccally, suppositories, ear and eye preparations, vaginal capsules, aqueous suspensions (lotions, shake mixtures), lipophilic suspensions, ointments, creams, milk, pastes, dusting powders, implants or stents.

In a preferred embodiment, the pharmaceutical composition comprising a compound of formula (I) as defined above is provided in a form suitable for oral administration. In another preferred embodiment, the pharmaceutical composition comprising a compound of formula (I) as defined above is provided in a form suitable for intravenous administration.

The active component of formula (I) can be converted into the recited application forms in a manner known per se. This is carried out using inert non-toxic, pharmaceutically suitable excipients. These include, inter alia, carriers (for example microcrystalline cellulose), solvents (for example liquid polyethylene glycols), emulsifiers (for example sodium dodecyl sulphate), dispersing agents (for example polyvinylpyrrolidone), synthetic and natural biopolymers (for example albumin), stabilizers (for example antioxidants such as ascorbic acid), colorants (for example inorganic pigments such as iron oxides) or taste and/or odor corrigents.

In another embodiment, the invention provides a method of treating a cell proliferative disorder in a patient in need of such treatment, comprising administering to the patient an effective amount of a compound of formula (I) as defined above. In certain embodiments, the cell proliferative disorder is cancer.

In still another aspect, the invention provides use of a compound of formula (I) as defined above for manufacturing a pharmaceutical composition for the treatment or prevention of a cell proliferative disorder. In certain embodiments, the cell proliferative disorder is cancer.

When the compounds of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically-acceptable carrier.

Regardless of the route of administration selected, the compounds of the invention, which may be used in a suitable hydrated form, and/or the pharmaceutical compositions of the present invention, are formulated into pharmaceutically-acceptable dosage forms by conventional methods known to those of skill in the art.

Actual dosage levels and time course of administration of the active ingredients in the pharmaceutical compositions of the invention may be varied so as to obtain an amount of the active ingredient which is effective to achieve the desired therapeutic response for a particular patient, composition, and mode of administration, without being toxic to the patient. An exemplary dose range is from 0.01 to 100 mg/kg per day or 0.1 to 150 mg/kg per day.

In certain embodiments, the compound of the invention can be used in combination therapy with conventional cancer chemotherapeutics. Conventional treatment regimens for leukemia and for other tumors include radiation, drugs, or a combination of both.

Determination of a therapeutically effective anti-proliferative amount or a prophylactically effective anti-proliferative amount of the compounds of the invention can be readily made by the physician or veterinarian (the "attending clinician"), as one skilled in the art, by the use of known techniques and by observing results obtained under analogous circumstances. The dosages may be varied depending upon the requirements of the patient in the judgment of the attending clinician; the severity of the condition being treated and the particular compound being employed. In determining the therapeutically effective anti-proliferative amount or dose, and the prophylactically effective anti-proliferative amount or dose, a number of factors are considered by the attending clinician, including, but not limited to: the specific cell proliferative disorder involved; pharmacodynamic characteristics of the particular agent and its mode and route of administration; the desired time course of treatment; the species of mammal; its size, age, and general health; the specific disease involved; the degree of or involvement or the severity of the disease; the response of the individual patient; the particular compound administered; the mode of administration; the bioavailability characteristics of the preparation administered; the dose regimen selected; the kind of concurrent treatment (i.e., the interaction of the compound of the invention with other co-administered therapeutics); and other relevant circumstances.

Treatment can be initiated with smaller dosages, which are less than the optimum dose of the compound. Thereafter, the dosage may be increased by small increments until the optimum effect under the circumstances is reached. For convenience, the total daily dosage may be divided and administered in portions during the day if desired. A therapeutically effective anti-proliferative amount and a prophylactically effective anti-proliferative amount of a compound of the invention may be expected to vary from about 0.01 milligram per kilogram of body weight per day (mg/kg/day) to about 100 mg/kg/day.

A preferred dose of the compound of the invention for the present invention is the maximum that a patient can tolerate and not develop serious side effects. Illustratively, the compound of the present invention is administered at a dose of about 0.01 mg/kg to about 100 mg/kg of body weight, about 0.01 mg/kg to about 10 mg/kg of body weight or about 0.1 mg/kg to about 10 mg/kg of body weight. Ranges intermediate to the above-recited values are also intended to be part of the invention.

The percentages in the tests and examples which follows are, unless otherwise stated, by weight; parts are by weight. Solvent ratios, dilution ratios and concentrations reported for liquid/liquid solutions are each based on volume.

A. EXAMPLES

Abbreviations and Acronyms:
Ac acetyl
aq. aqueous (solution)
br. s broad singlet (NMR)
cat. catalytic
conc. concentrated
d doublet (NMR)
DCI direct chemical ionization (MS)
dd doublet of doublets (NMR)
DMF N,N-dimethylformamide
DMSO dimethylsulfoxide
DMSO-$d_6$ dimethylsulfoxide-$d_6$
EI electron impact ionization (MS)
equiv. equivalent(s)
ESI electro-spray ionization (MS)
Et ethyl
GC-MS gas chromatography-coupled mass spectrometry
h hour(s)
$^1$H-NMR proton nuclear magnetic resonance spectrometry
HOAc acetic acid
HPLC high performance/high pressure liquid chromatography
LC-MS liquid chromatography-coupled mass spectrometry
m multiplet (NMR)
Me methyl
min minute(s)
MS mass spectrometry
m/z mass-to-charge ratio
of th. of theory (chemical yield)
Ph phenyl
q quartet (NMR)
$R_f$ TLC retention factor
RP reverse phase (HPLC)
rt room temperature
$R_t$ retention time (HPLC)
s singlet (NMR)
sept septet (NMR)
tBu tert-butyl
TFA trifluoroacetic acid
THF tetrahydrofuran
TLC thin layer chromatography
t triplet (NMR)
v/v volume-to-volume ratio
w/v weight-to-volume ratio
w/w weight-to-weight ratio
LC-MS and GC-MS Methods:
Method 1 (LC-MS):
Instrument: Micromass ZQ with HPLC Waters Alliance 2795; column: Phenomenex Synergi 2.5 µMAX-RP 100A Mercury, 20 mm×4 mm; eluent A: 1 L water+0.5 mL 50% formic acid, eluent B: 1 L acetonitrile+0.5 mL-50% formic acid; gradient: 0.0 min 90% A→0.1 min 90% A→3.0 min 5% A→4.0 min 5% A→4.01 min 90% A; flow rate: 2 mL/min; oven: 50° C.; UV detection: 210 nm.
Method 2 (LC-MS):
Instrument: Micromass Quattro Premier with HPLC Waters UPLC Acquity; column: Thermo Hypersil GOLD 1.9µ, 50 mm×1 mm; eluent A: 1 L water+0.5 mL 50% formic acid, eluent B: 1 L acetonitrile+0.5 mL 50% formic acid; gradient: 0.0 min 90% A→0.1 min 90% A→1.5 min 10% A→2.2 min 10% A; oven: 50° C.; flow rate: 0.33 mL/min; UV detection: 210 nm
Method 3 (LC-MS):
Instrument: Micromass Quattro Micro with HPLC Agilent 1100 Series; column: Thermo Hypersil GOLD 3µ, 20 mm×4 mm; eluent A: 1 L water+0.5 mL 50% formic acid, eluent B: 1 L acetonitrile+0.5 mL 50% formic acid; gradient: 0.0 min 100% A→3.0 min 10% A→4.0 min 10% A→4.01 min 100% A (flow rate 2.5 mL/min)→5.00 min 100% A; oven: 50° C.; flow rate: 2 mL/min; UV detection: 210 nm.
Method 4 (LC-MS):
Instrument: Waters Acquity SQD UPLC System; column: Waters Acquity UPLC HSS T3 1.8µ, 50 mm×1 mm; eluent A: 1 L water+0.25 mL 99% formic acid, eluent B: 1 L acetonitrile+0.25 mL 99% formic acid; gradient: 0.0 min 90% A→1.2 min 5% A→2.0 min 5% A; oven: 50° C.; flow rate: 0.40 mL/min; UV detection: 210-400 nm
Method 5 (GC-MS):
Instrument: Micromass GCT, GC 6890; column. Restek RTX-35, 15 m×200 µm×0.33 µm; constant flow with helium: 0.88 mL/min; oven: 70° C.; inlet: 250° C.; gradient: 70° C., 30° C./min→310° C. (keep for 3 min)

Starting Materials and Intermediates

Example 1A

Furo[3,2-c]pyridin-4-amine

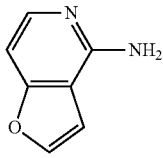

65.3 g (425 mmol) 4-chlorofuro[3,2-c]pyridine [CAS Reg.-No. 31270-80-1] were suspended in 600 ml aqueous ammonia solution (35%) in an autoclave. After addition of 2 g copper(I)-chloride, the reaction mixture was stirred for 20 h at 150° C. After cooling to rt, the mixture was extracted with dichloromethane (3×400 ml). The combined organic phases were washed with brine, dried over magnesium sulfate, filtered, and concentrated under reduced pressure to yield 46.6 g (82% of th.) of crude title compound (content >95% by GC) which was used in the next step without further purification.

Example 2A

N-(Furo[3,2-c]pyridin-4-yl)benzamide

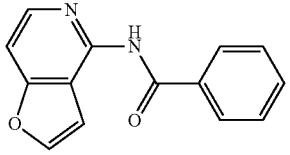 [SMILES: O=C(Nc1nccc2occc12)c1ccccc1]

42.2 g (315 mmol) furo[3,2-c]pyridin-4-amine (Example 1A) were dissolved in 500 ml dry pyridine. After addition of 71.3 g (315 mmol) benzoic acid anhydride in portions, the reaction mixture was heated to reflux for 3 h. After cooling to rt, the mixture was poured into 5000 ml of water. The resulting precipitate was filtered off, washed with water, and dried to afford 71.3 g (95% of th.) of the title compound as a brownish solid which was used in the next step without further purification [cf. J. B. M. Rewinkel et al., *Bioorg. Med. Chem. Lett.* 9, 2837-2842 (1999)].

LC-MS (method 4): $R_t$=0.67 min; MS (ESIpos): m/z=239 (M+H)$^+$ $^1$H-NMR (400 MHz, DMSO-d$_6$): δ=11.03 (s, 1H), 8.30 (d, 1H), 8.11-8.02 (m, 3H), 7.63 (m, 1H), 7.60-7.50 (m, 3H), 6.92 (s, 1H) ppm.

Example 3A

N-(2-Formylfuro[3,2-c]pyridin-4-yl)benzamide

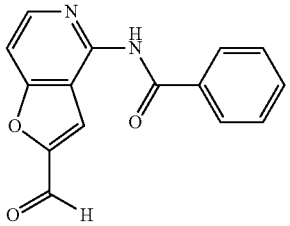 [SMILES: O=Cc1cc2c(NC(=O)c3ccccc3)nccc2o1]

7.13 g (30 mmol) N-(Furo[3,2-c]pyridin-4-yl)benzamide (Example 2A) were dissolved in 150 ml dry THF under inert gas atmosphere. At −78° C., 26.4 ml (66 mmol) n-butyl-lithium solution (2.5 M in hexane) were added dropwise, and the mixture was stirred for 30 min at this temperature. Then, 5.1 ml (66 mmol) dry N,N-dimethylformamide were added dropwise. After addition was completed, the mixture was slowly warmed up to rt, and 300 ml saturated aq. ammonium chloride solution were added. After extraction with 300 ml diethyl ether, the organic phase was dried over magnesium sulfate, filtered, and concentrated under reduced pressure to afford a brown solid. This material was purified by chromatography on silica gel (eluent dichloromethane/methanol 99:1 v/v) to afford 5.2 g (65% of th.) of the title compound as a pale yellow solid [cf. J. B. M. Rewinkel et al., *Bioorg. Med. Chem. Lett.* 9, 2837-2842 (1999)].

LC-MS (method 4): $R_t$=0.80 min; MS (ESIpos): m/z=267 (M+H)$^+$ $^1$H-NMR (400 MHz, DMSO-d$_6$): δ=11.34 (s, 1H), 9.90 (s, 1H), 8.49 (d, 1H), 8.11 (m, 2H), 8.01 (s, 1H), 7.70-7.62 (m, 2H), 7.57 (m, 2H) ppm.

Example 4A

N-{2-(2-Cyano-3-oxobut-1-en-1-yl)furo[3,2-c]pyridin-4-yl}benzamide

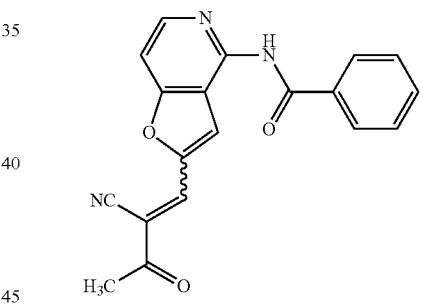

A mixture of 1.50 g (5.63 mmol) N-(2-formylfuro[3,2-c]pyridin-4-yl)benzamide (Example 3A), 0.65 g (6.2 mmol) sodium (1Z)-1-cyanoprop-1-en-2-olate, 0.4 ml (7.04 mmol) acetic acid and 56 μl (0.56 mmol) piperidine in dry dichloromethane (35 ml) containing 4 Å molecular sieve was stirred under reflux for 1 h. After cooling, 50 ml aq. sodium bicarbonate solution were added, and the mixture was stirred for 1 h at rt. The molecular sieve was filtered off, and the filtrate was concentrated under reduced pressure. The residue was treated with ethyl acetate and saturated aq. sodium carbonate solution. The organic layer was separated, washed with water, dried, and concentrated under reduced pressure to afford the title compound (1.5 g, 80% of th.) as a pale yellow solid which was used in the next step without further purification.

LC-MS (method 3): $R_t$=1.91 min; MS (ESIpos): m/z=332 (M+H)$^+$ $^1$H-NMR (400 MHz, DMSO-d$_6$): δ=11.34 (br. s, 1H), 8.47 (d, 1H), 8.41 (s, 1H), 8.11 (m, 2H), 7.93 (s, 1H), 7.66 (m, 2H), 7.57 (m, 2H), 2.55 (br. m, 3H) ppm.

Example 5A

3-Amino-3-(4-fluorophenyl)prop-2-enenitrile

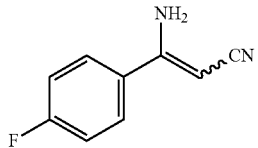 [SMILES: N#CC=C(N)c1ccc(F)cc1]

A solution of 0.390 ml (2.78 mmol) diisopropylamine in dry THF (2 ml) was cooled to −70° C. under inert gas atmosphere, and 1.74 ml (2.78 mmol) n-butyllithium solution (1.6 M in hexanes) were added dropwise. Then, a solution of 129 μl (2.45 mmol) acetonitrile in dry THF (2 ml) was slowly added over 10 min. The resulting solution was stirred for further 30 min at −70° C. before a solution of 200 mg (1.635 mmol) 4-fluorobenzonitrile in dry THF (2 ml) was added. The mixture was allowed to warm to room temperature and stirred for 1 h before water (4 ml) was added slowly. The mixture was extracted several times with dichloromethane (50 ml). The combined organic layers were dried over sodium sulfate and concentrated under reduced pressure to yield 244 mg (92% of th.) of the crude title compound which was used in the next step without further purification.

LC-MS (method 4): $R_t$=0.81 min; MS (ESIpos): m/z=163 (M+H)$^+$.

Example 6A

3-Amino-3-(4-chlorophenyl)prop-2-enenitrile

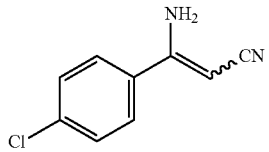 [SMILES: N#CC=C(N)c1ccc(Cl)cc1]

The title compound was prepared following the procedure described in Example 5A using 4-chlorobenzonitrile (500 mg, 3.598 mmol) to yield 598 mg (93% of th.) of the crude product which was used in the next step without further purification.

GC-MS (method 5): $R_t$=6.38 min; MS (EIpos): m/z=178 (M)$^+$.

Example 7A

5-Methoxy-3,6-dihydro-2H-1,4-oxazine

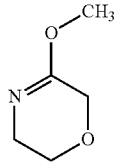

A solution of 1.2 g (11.9 mmol) morpholine-3-one in dichloromethane (70 ml) was cooled to 0° C. and treated with 25 g (238 mmol) dry sodium carbonate. After stirring for 10 min at 0° C., 6.14 g (41.5 mmol) trimethyloxonium tetrafluoroborate were added at 0° C. The mixture was allowed to warm to room temperature and stirred for 6 h. Water (100 ml) was added, and the organic layer was separated. The aqueous phase was extracted several times with dichloromethane, and the combined organic layers were washed with brine, dried over sodium sulfate and concentrated under reduced pressure. The crude product thus obtained was used in the next step without further purification.

GC-MS (method 5): $R_t$=3.36 min; MS (ESIpos): m/z=116 (M+H)$^+$.

Example 8A tert-Butyl (2E/Z)-cyano(morpholin-3-ylidene)ethanoate

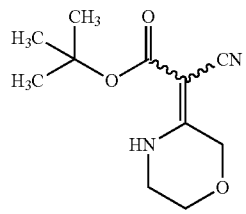

A mixture of 0.48 g (4.17 mmol) 5-methoxy-3,6-dihydro-2H-1,4-oxazine (Example 7A) and 0.61 g (4.34 mmol) tert-butyl cyanoacetate in THF (25 ml) was stirred under reflux for 12 h. The mixture was then cooled to room temperature and concentrated under reduced pressure. The residue was purified by flash chromatography (silica gel, eluent cyclohexane/ethyl acetate 3:1) to yield the title compound as a white solid (0.269 g, 27% of th.).

LC-MS (method 2): $R_t$=0.99 min; MS (ESIpos): m/z=225 (M+H)$^+$ $^1$H-NMR (400 MHz, DMSO-d$_6$): δ=10.02 (br. s, 1H), 4.47 (s, 2H), 3.84 (t, 2H), 3.37 (m, 2H), 1.44 (s, 9H) ppm.

PREPARATION EXAMPLES

Example 1

N-{2-[3,5-Dicyano-2-(difluoromethyl)-6-methyl-1,4-dihydropyridin-4-yl]furo[3,2-c]pyridin-4-yl}-benzamide

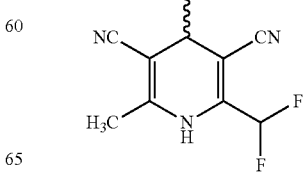

A mixture of 200 mg (0.604 mmol) N-{2-(2-cyano-3-oxobut-1-en-1-yl)furo[3,2-c]pyridin-4-yl}benzamide (Example 4A) and 285 mg (2.41 mmol) 3-amino-4,4-difluorobut-2-enenitrile [obtainable by Thorpe reaction of acetonitrile with 2,2-difluoroacetonitrile, cf. *Org. React.* 15, 1 (1967), ibid. 31, 1 (1984)] in 2-propanol (1 ml) was stirred at reflux for 12 h. Upon cooling, the mixture was concentrated under reduced pressure, and the residue was directly purified by preparative RP-HPLC (acetonitrile/water+0.1% TFA gradient, final mixture 90:10 v/v) to yield 176 mg (67% of th.) of the racemic title compound.

LC-MS (method 2): $R_t$ =0.97 min; MS (ESIpos): m/z=432 (M+H)$^+$ $^1$H-NMR (400 MHz, DMSO-d$_6$): δ=11.40 (br. s, 1H), 10.37 (s, 1H), 8.36 (d, 1H), 8.08 (m, 2H), 7.72 (m, 1H), 7.67 (m, 1H), 7.57 (m, 2H), 7.12 (s, 1H), 6.87 (t, 1H, $^2J_{H-F}$=51.8 Hz), 5.24 (s, 1H), 2.15 (s, 3H) ppm.

Example 2

N-{2-[3,5-Dicyano-2-(4-fluorophenyl)-6-methyl-1,4-dihydropyridin-4-yl]furo[3,2-c]pyridin-4-yl}-benzamide

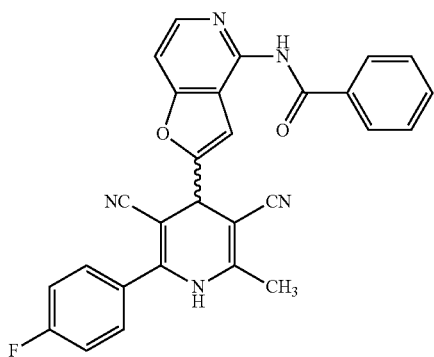 [SMILES: CC1=C(C#N)C(c2cc3c(NC(=O)c4ccccc4)nccc3o2)C(C#N)=C(c2ccc(F)cc2)N1]

A mixture of 200 mg (0.604 mmol) N-{2-(2-cyano-3-oxobut-1-en-1-yl)furo[3,2-c]pyridin-4-yl}benzamide (Example 4A) and 117 mg (0.724 mmol) 3-amino-3-(4-fluorophenyl)prop-2-enenitrile (Example 5A) in acetic acid (2 ml) was stirred for 30 min at 110° C. Upon cooling, the mixture was concentrated under reduced pressure, and the residue was directly purified by preparative RP-HPLC (acetonitrile/water+0.1% TFA gradient, final mixture 90:10 v/v) to yield 235 mg (82% of th.) of the racemic title compound.

LC-MS (method 4): $R_t$=0.99 min; MS (ESIpos): m/z=476 (M+H)$^+$ $^1$H-NMR (400 MHz, DMSO-d$_6$): δ=11.32 (br. s, 1H), 10.02 (s, 1H), 8.35 (d, 1H), 8.09 (m, 2H), 7.73-7.62 (m, 4H), 7.57 (m, 2H), 7.45-7.35 (m, 2H), 7.08 (s, 1H), 5.16 (s, 1H), 2.15 (s, 3H) ppm.

Example 3

N-{2-[3,5-Dicyano-2-(4-chlorophenyl)-6-methyl-1,4-dihydropyridin-4-yl]furo[3,2-c]pyridin-4-yl}-benzamide

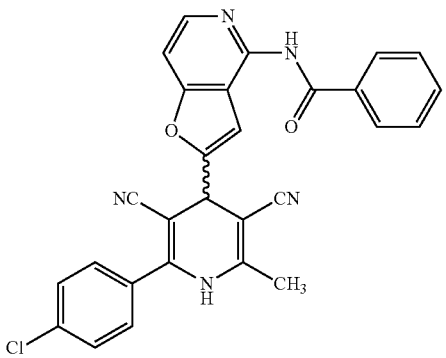 [SMILES: CC1=C(C#N)C(c2cc3c(NC(=O)c4ccccc4)nccc3o2)C(C#N)=C(c2ccc(Cl)cc2)N1]

A mixture of 200 mg (0.604 mmol) N-{2-(2-cyano-3-oxobut-1-en-1-yl)furo[3,2-c]pyridin-4-yl}benzamide (Example 4A) and 129 mg (0.724 mmol) 3-amino-3-(4-chlorophenyl)prop-2-enenitrile (Example 6A) in acetic acid (2 ml) was stirred for 30 min at 110° C. Upon cooling, the mixture was concentrated under reduced pressure, and the residue was directly purified by preparative RP-HPLC (acetonitrile/water+0.1% TFA gradient, final mixture 90:10 v/v) to yield 197 mg (64% of th.) of the racemic title compound.

LC-MS (method 4): $R_t$=1.04 min; MS (ESIpos): m/z=492 (M+H)$^+$ $^1$H-NMR (400 MHz, DMSO-d$_6$): δ=11.29 (br. s, 1H), 10.04 (s, 1H), 8.35 (d, 1H), 8.09 (m, 2H), 7.73-7.61 (m, 6H), 7.57 (m, 2H), 7.06 (s, 1H), 5.16 (s, 1H), 2.15 (s, 3H) ppm.

Example 4

N-[2-(3,5-Dicyano-2,6-dimethyl-1,4-dihydropyridin-4-yl)furo[3,2-c]pyridin-4-yl]benzamide

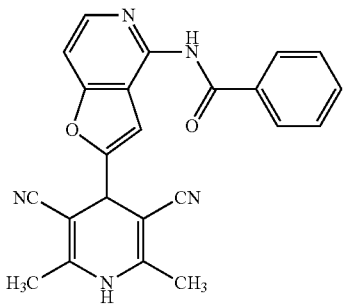 [SMILES: CC1=C(C#N)C(c2cc3c(NC(=O)c4ccccc4)nccc3o2)C(C#N)=C(C)N1]

A mixture of 69 mg (0.260 mmol) N-(2-formylfuro[3,2-c]pyridin-4-yl)benzamide (Example 3A) and 43 mg (0.52 mmol) (2Z)-3-aminobut-2-enenitrile in acetic acid (4.5 ml) was stirred for 45 min at 110° C. Upon cooling, the reaction mixture was concentrated under reduced pressure, and the residue was treated with ethyl acetate and saturated aq. sodium carbonate solution. The organic layer was separated, washed with brine and water, dried over sodium sulfate, and concentrated under reduced pressure to afford the title compound (45 mg, 43% of th.) as a pale yellow solid.

LC-MS (method 4): $R_t$=0.84 min; MS (ESIpos): m/z=396 (M+H)$^+$ $^1$H-NMR (400 MHz, DMSO-d$_6$): δ=11.05 (s, 1H), 9.74 (s, 1H), 8.30 (d, 1H), 8.09 (m, 2H), 7.65-7.50 (m, 4H), 6.80 (s, 1H), 4.94 (s, 1H), 2.07 (s, 6H) ppm.

Example 5

4-(4-Aminofuro[3,2-c]pyridin-2-yl)-2,6-dimethyl-1,4-dihydropyridine-3,5-dicarbonitrile

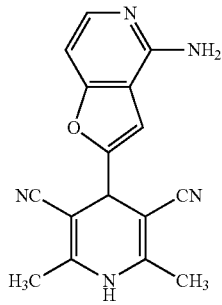 [SMILES: CC1=C(C#N)C(c2cc3c(N)nccc3o2)C(C#N)=C(C)N1]

A solution of 43 mg (0.11 mmol) N-[2-(3,5-dicyano-2,6-dimethyl-1,4-dihydropyridin-4-yl)furo[3,2-c]pyridin-4-yl]benzamide (Example 4) in acetic acid (3 ml) was treated with 0.2 ml hydrochloric acid (37%) and stirred for 24 h at 100° C. Then, further 0.2 ml hydrochloric acid (37%) were added, and stirring was continued for 48 h at 100° C. Upon cooling, saturated aq. sodium carbonate solution was added until a neutral pH was reached. The mixture was extracted with ethyl acetate, and the organic layer was washed with brine and water, dried over sodium sulfate, and concentrated under reduced pressure. The crude product was purified by preparative thin layer chromatography (silica, eluent dichloromethane/methanol 10:1 v/v) to afford the title compound (5.6 mg, 18% of th.) as a white solid.

LC-MS (method 4): $R_t$=0.54 min; MS (ESIpos): m/z=292 (M+H)$^+$ $^1$H-NMR (400 MHz, DMSO-d$_6$): δ=9.68 (s, 1H), 7.77 (d, 1H), 6.88 (s, 1H), 6.79 (d, 1H), 6.48 (s, 2H), 4.81 (s, 1H), 2.06 (s, 6H) ppm.

Example 6

4-(4-Aminofuro[3,2-c]pyridin-2-yl)-2-(difluoromethyl)-6-methyl-1,4-dihydropyridine-3,5-dicarbonitrile

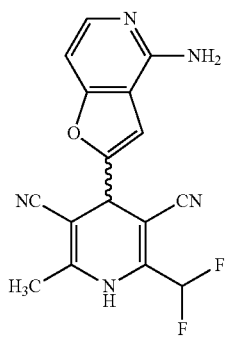 [SMILES: CC1=C(C#N)C(c2cc3c(N)nccc3o2)C(C#N)=C(C(F)F)N1]

The title compound was prepared from 176 mg (0.41 mmol) N-{2-[3,5-dicyano-2-(difluoromethyl)-6-methyl-1,4-dihydropyridin-4-yl]furo[3,2-c]pyridin-4-yl}benzamide (Example 1) following the procedure described in Example 5 to yield 22 mg (16% of th.) of the racemic product after purification by RP-HPLC (methanol/water+0.1% TFA gradient, final mixture 100% methanol).

LC-MS (method 4): $R_t$=0.56 min; MS (ESIpos): m/z=328 (M+H)$^+$ $^1$H-NMR (400 MHz, DMSO-d$_6$): δ=10.28 (s, 1H), 7.79 (d, 1H), 6.97 (s, 1H), 6.86 (t, 1H, $^2J_{H,F}$=51.84 Hz), 6.81 (d, 1H), 6.54 (br. s, 2H), 5.06 (s, 1H), 2.13 (s, 3H) ppm.

Example 7

N-{2-[3,5-Dicyano-2-methyl-6-(trifluoromethyl)-1,4-dihydropyridin-4-yl]furo[3,2-c]pyridin-4-yl}-benzamide

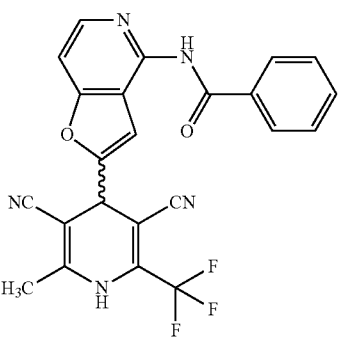 [SMILES: CC1=C(C#N)C(c2cc3c(NC(=O)c4ccccc4)nccc3o2)C(C#N)=C(C(F)(F)F)N1]

A mixture of 200 mg (0.604 mmol) N-{2-(2-cyano-3-oxobut-1-en-1-yl)furo[3,2-c]pyridin-4-yl}-benzamide (Example 4A) and 329 mg (2.41 mmol) (2E)-3-amino-4,4,4-trifluorobut-2-enenitrile [CAS Reg.-No. 33561-24-9; prepared following A. W. Lutz, U.S. Pat. No. 3,635,977 and also C. G. Krespan, *J. Org. Chem.* 34, 42-45 (1969)] in 2-propanol (1 ml) was stirred at reflux for 12 h. Upon cooling, the mixture was concentrated under reduced pressure, and the residue was directly purified by preparative RP-HPLC (acetonitrile/water+0.1% TFA gradient, final mixture 90:10 v/v) to yield 171 mg (63% of th.) of the racemic title compound.

LC-MS (method 4): $R_t$=0.95 min; MS (ESIpos): m/z=450 (M+H)$^+$ $^1$H-NMR (400 MHz, DMSO-d$_6$): δ=11.29 (br. s, 1H), 10.59 (s, 1H), 8.36 (d, 1H), 8.09 (m, 2H), 7.72-7.62 (m, 2H), 7.57 (m, 2H), 7.09 (s, 1H), 5.31 (s, 1H), 2.17 (s, 3H) ppm.

Example 8

4-(4-Aminofuro[3,2-c]pyridin-2-yl)-2-methyl-6-(trifluoromethyl)-1,4-dihydropyridine-3,5-dicarbonitrile

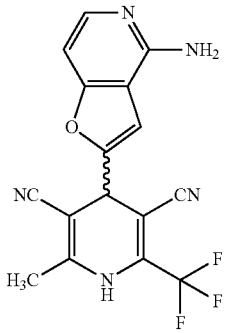 [SMILES: CC1=C(C#N)C(c2cc3c(N)nccc3o2)C(C#N)=C(C(F)(F)F)N1]

The title compound was prepared from 140 mg (0.31 mmol) N-{2-[3,5-dicyano-2-methyl-6-(trifluoromethyl)-1,4-dihydropyridin-4-yl]furo[3,2-c]pyridin-4-yl}benzamide (Example 7) following the procedure described in Example 5 to yield 29 mg (27% of th.) of the racemic product after purification by RP-HPLC (methanol/water+0.1% TFA gradient, final mixture 100% methanol).

LC-MS (method 4): $R_t$=0.62 min; MS (ESIpos): m/z=346 $(M+H)^+$ $^1$H-NMR (400 MHz, DMSO-$d_6$): δ=10.64 (br. s, 1H), 7.80 (d, 1H), 7.02 (s, 1H), 6.84 (d, 1H), 6.64 (br. s, 2H), 5.15 (s, 1H), 2.15 (s, 3H) ppm.

Example 9

4-(4-Aminofuro[3,2-c]pyridin-2-yl)-2-(4-fluorophenyl)-6-methyl-1,4-dihydropyridine-3,5-dicarbonitrile

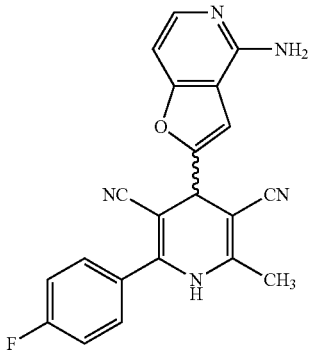 [SMILES: CC1=C(C#N)C(c2cc3c(N)nccc3o2)C(C#N)=C(c2ccc(F)cc2)N1]

The title compound was prepared from 235 mg (0.494 mmol) N-{2-[3,5-dicyano-2-(4-fluorophenyl)-6-methyl-1,4-dihydropyridin-4-yl]furo[3,2-c]pyridin-4-yl}benzamide (Example 2) following the procedure described in Example 5 to yield 52.4 mg (28% of th.) of the racemic product after purification by RP-HPLC (methanol/water+0.1% TFA gradient, final mixture 100% methanol).

LC-MS (method 4): $R_t$=0.69 min; MS (ESIpos): m/z=372 $(M+H)^+$ $^1$H-NMR (400 MHz, DMSO-$d_6$): δ=9.96 (s, 1H), 7.79 (d, 1H), 7.65 (m, 2H), 7.40 (m, 2H), 7.01 (s, 1H), 6.86 (d, 1H), 6.66 (br. s, 2H), 4.98 (s, 1H), 2.13 (s, 3H) ppm.

Example 10

4-(4-Aminofuro[3,2-c]pyridin-2-yl)-2-(4-chlorophenyl)-6-methyl-1,4-dihydropyridine-3,5-dicarbonitrile

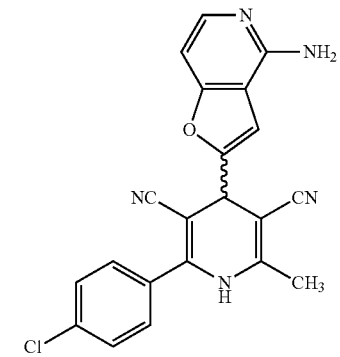 [SMILES: CC1=C(C#N)C(c2cc3c(N)nccc3o2)C(C#N)=C(c2ccc(Cl)cc2)N1]

The title compound was prepared from 197 mg (0.40 mmol) N-{2-[3,5-dicyano-2-(4-chlorophenyl)-6-methyl-1,4-dihydropyridin-4-yl]furo[3,2-c]pyridin-4-yl}benzamide (Example 3) following the procedure described in Example 5 to yield 47 mg (30% of th.) of the racemic product after purification by RP-HPLC (methanol/water+0.1% TFA gradient, final mixture 100% methanol).

LC-MS (method 4): $R_t$=0.75 min; MS (ESIpos): m/z=388 $(M+H)^+$ $^1$H-NMR (400 MHz, DMSO-$d_6$): δ=10.09 (s, 1H), 8.51 (br. s, 2H), 7.89 (d, 1H), 7.64 (m, 4H), 7.35 (d, 1H), 7.33 (s, 1H), 5.20 (s, 1H), 2.15 (s, 3H) ppm.

Example 11

N-{2-[3,5-Dicyano-2,6-bis(difluoromethyl)-1,4-dihydropyridin-4-yl]furo[3,2-c]pyridin-4-yl}benzamide

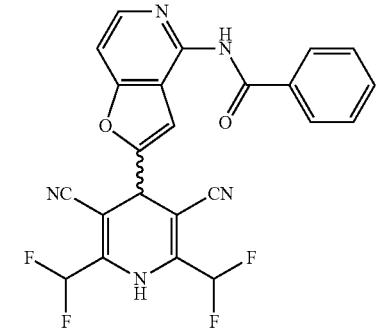 [SMILES: N#CC1=C(C(F)F)NC(C(F)F)=C(C#N)C1c1cc2c(NC(=O)c3ccccc3)nccc2o1]

A solution of 200 mg (0.75 mmol) N-(2-formylfuro[3,2-c]pyridin-4-yl)benzamide (Example 3A) in acetic acid (1.3 ml) was treated with a solution of 200 mg (1.69 mmol) 3-amino-4,4-difluorobut-2-enenitrile [obtainable by Thorpe reaction of acetonitrile with 2,2-difluoroacetonitrile, cf. *Org. React.* 15, 1 (1967), *ibid.* 31, 1 (1984)] in 1-butanol (1.0 ml). The mixture was heated to reflux temperature for 2 h. Upon cooling, the reaction mixture was concentrated under reduced pressure, and the residue was treated with ethyl acetate and saturated aq. sodium bicarbonate solution. The organic layer was separated, washed with brine and with water, dried over sodium sulfate, and concentrated under reduced pressure. The residue was purified by preparative RP-HPLC (methanol/water+0.1% TFA gradient, final mixture 100% methanol) yielding 28 mg (8% of th.) of the title compound.

LC-MS (method 4): $R_t$=0.94 min; MS (ESIpos): m/z=468 (M+H)$^+$ $^1$H-NMR (400 MHz, DMSO-d$_6$): δ=11.29 (br. s, 1H), 11.02 (br. s, 1H), 8.36 (d, 1H), 8.09 (m, 2H), 7.67 (m, 2H), 7.56 (m, 2H), 7.11 (s, 1H), 6.89 (t, 2H), 5.43 (s, 1H) ppm.

Example 12

N-[2-(7,9-Dicyano-6-methyl-1,3,4,8-tetrahydropyrido[2,1-c][1,4]oxazin-8-yl)furo[3,2-c]pyridin-4-yl]benzamide

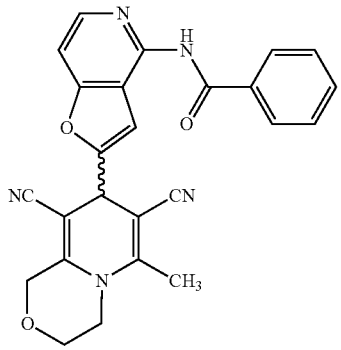 [SMILES: CC1=C(C#N)C(c2cc3c(NC(=O)c4ccccc4)nccc3o2)C(C#N)=C2COCCN12]

A mixture of 162 mg (0.724 mmol) tert-butyl (2E/Z)-cyano(morpholin-3-ylidene)ethanoate (Example 8A) in 6 M hydrochloric acid (21 ml) was heated to 100° C. for 1 h. After cooling to room temperature, the solution was concentrated under reduced pressure, and the remaining solid was dissolved in acetic acid (4 ml). 200 mg (0.604 mmol) N-{2-(2-cyano-3-oxobut-1-en-1-yl)furo[3,2-c]-pyridin-4-yl}benzamide (Example 4A) were added, and the mixture was stirred at 100° C. for 0.5 h. Upon cooling, the reaction mixture was concentrated under reduced pressure, and the residue was treated with ethyl acetate and saturated aq. sodium bicarbonate solution. The organic layer was separated, washed with brine and with water, dried over sodium sulfate, and concentrated under reduced pressure. The residue was purified by preparative RP-HPLC (methanol/water+0.1% TFA gradient, final mixture 100% methanol) yielding 161 mg (58% of th.) of the racemic title compound.

LC-MS (method 4): $R_t$=0.87 min; MS (ESIpos): m/z=438 (M+H)$^+$ $^1$H-NMR (400 MHz, DMSO-d$_6$): δ=11.30 (br. s, 1H), 8.34 (d, 1H), 7.66 (m, 2H), 7.57 (m, 2H), 7.00 (s, 1H), 5.07 (s, 1H), 4.63-4.51 (m, 2H), 4.0-3.6 (m, 4H), 2.28 (s, 3H) ppm.

Example 13

N-[2-(5-Cyano-3,6-dimethyl-4,7-dihydro[1,2]oxazolo[5,4-b]pyridin-4-yl)furo[3,2-c]pyridin-4-yl]benzamide

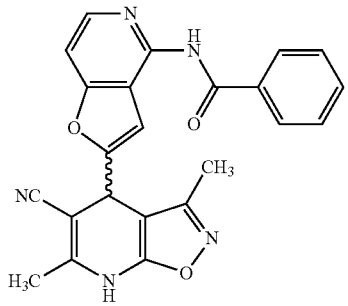 [SMILES: CC1=C(C#N)C(c2cc3c(NC(=O)c4ccccc4)nccc3o2)c2c(C)noc2N1]

A mixture of 200 mg (0.604 mmol) N-{2-(2-cyano-3-oxobut-1-en-1-yl)furo[3,2-c]pyridin-4-yl}benzamide (Example 4A), 59 mg (0.604 mmol) 3-methyl-1,2-oxazol-5-amine and a trace amount of powdered 4 Å molecular sieve in 2-propanol (2 ml) was stirred at 90° C. for 12 h. Upon cooling, the mixture was concentrated under reduced pressure, and the residue was directly purified by preparative RP-HPLC (methanol/water+0.1% TFA gradient, final mixture 100% methanol) to yield 64 mg (26% of th.) of the racemic title compound.

LC-MS (method 3): $R_t$=1.68 min; MS (ESIpos): m/z=412 (M+H)$^+$ $^1$H-NMR (400 MHz, DMSO-d$_6$): δ=11.3 (br. s, 1H), 11.1 (s, 1H), 8.31 (d, 1H), 8.08 (m, 2H), 7.66 (m, 2H), 7.56 (m, 2H), 6.96 (s, 1H), 5.41 (s, 1H), 2.18 (s, 3H), 1.97 (s, 3H) ppm.

Example 14

N-[2-(3-Cyano-2-methyl-5-oxo-1,4,5,7-tetrahydrofuro[3,4-b]pyridin-4-yl)furo[3,2-c]pyridin-4-yl]benzamide

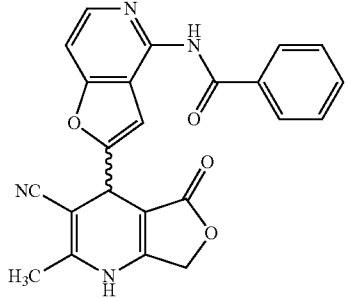 [SMILES: CC1=C(C#N)C(c2cc3c(NC(=O)c4ccccc4)nccc3o2)C2=C(COC2=O)N1]

A solution of 200 mg (0.75 mmol) N-(2-formylfuro[3,2-c]pyridin-4-yl)benzamide (Example 3A), 85 mg (1.033 mmol) 3-aminobut-2-enenitrile and 177 mg (0.939 mmol) ethyl 4-(acetoxy)-3-oxobutanoate [Tetrahedron 1978, 34, 1453-1455] in 1-propanol (4 ml) was stirred at 90° C. for 12 h. Then, concentrated hydrochloric acid (185 µl) and water (560 µl) were added, and stirring was continued for 20 min at 100° C. Upon cooling, the reaction mixture was concentrated under reduced pressure, and the residue was treated with ethyl acetate and saturated aq. sodium bicarbonate solution. The organic layer was separated, washed with brine and with water, dried over sodium sulfate, and concentrated under reduced pressure. The residue was purified by preparative RP-HPLC (methanol/water+0.1% TFA gradient, final mixture 100% methanol) yielding 96 mg (31% of th.) of the racemic title compound.

LC-MS (method 4): $R_t$=0.74 min; MS (ESIpos): m/z=413 (M+H)$^+$ $^1$H-NMR (400 MHz, DMSO-d$_6$): δ=11.02 (br. s, 1H), 10.37 (br. s, 1H), 8.28 (d, 1H), 8.08 (m, 2H), 7.63 (m, 1H), 7.54 (m, 3H), 6.75 (s, 1H), 5.05-4.85 (m, 3H), 2.15 (s, 3H) ppm.

Example 15

N-{2-[3-Cyano-2-(4-fluorophenyl)-5-oxo-1,4,5,7-tetrahydrofuro[3,4-b]pyridin-4-yl]furo[3,2-c]-pyridin-4-yl}benzamide

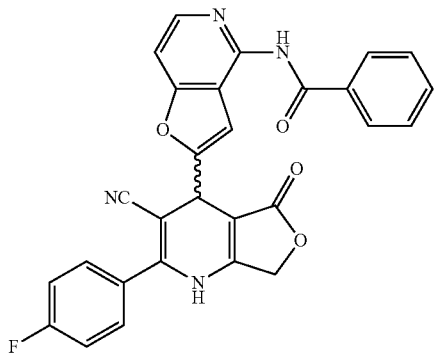 [SMILES: N#CC1=C(c2ccc(F)cc2)NC2=C(C(=O)OC2)C1c1cc2c(NC(=O)c3ccccc3)nccc2o1]

The title compound was prepared from 200 mg (0.75 mmol) N-(2-formylfuro[3,2-c]pyridin-4-yl)-benzamide (Example 3A), 167 mg (1.033 mmol) 3-amino-3-(4-fluorophenyl)prop-2-enenitrile (Example 5A) and 177 mg (0.939 mmol) ethyl 4-(acetoxy)-3-oxobutanoate [*Tetrahedron* 1978, 34, 1453-1455] following the procedure described in Example 14 to yield 193 mg (52% of th.) of the racemic product after purification by RP-HPLC (methanol/water+0.1% TFA gradient, final mixture 100% methanol).

LC-MS (method 4): $R_t$=0.89 min; MS (ESIpos): m/z=493 (M+H)$^+$ $^1$H-NMR (400 MHz, DMSO-d$_6$): δ=11.33 (br. s, 1H), 10.33 (br. s, 1H), 8.33 (d, 1H), 8.09 (m, 2H), 7.73-7.62 (m, 4H), 7.57 (m, 2H), 7.42 (m, 2H), 7.04 (s, 1H), 5.23 (s, 1H), 5.04-4.92 (m, 2H) ppm.

Example 16

N-{2-[3-Cyano-2-(4-chlorophenyl)-5-oxo-1,4,5,7-tetrahydrofuro[3,4-b]pyridin-4-yl]furo[3,2-c]-pyridin-4-yl}benzamide

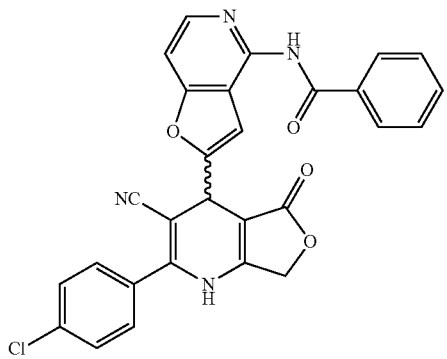 [SMILES: N#CC1=C(c2ccc(Cl)cc2)NC2=C(C(=O)OC2)C1c1cc2c(NC(=O)c3ccccc3)nccc2o1]

The title compound was prepared from 200 mg (0.75 mmol) N-(2-formylfuro[3,2-c]pyridin-4-yl)-benzamide (Example 3A), 184 mg (1.033 mmol) 3-amino-3-(4-chlorophenyl)prop-2-enenitrile (Example 6A) and 177 mg (0.939 mmol) ethyl 4-(acetoxy)-3-oxobutanoate [*Tetrahedron* 1978, 34, 1453-1455] following the procedure described in Example 14 to yield 124 mg (29% of th.) of the racemic product after purification by RP-HPLC (methanol/water+0.1% TFA gradient, final mixture 100% methanol).

LC-MS (method 2): $R_t$=1.04 min; MS (ESIpos): m/z=509 (M+H)$^+$ $^1$H-NMR (400 MHz, DMSO-d$_6$): δ=11.33 (br. s, 1H), 10.66 (s, 1H), 8.33 (d, 1H), 8.08 (m, 2H), 7.70-7.62 (m, 6H), 7.57 (m, 2H), 7.04 (s, 1H), 5.24 (s, 1H), 5.04-4.92 (m, 2H) ppm.

Example 17

N-[2-(3,5-Dicyano-1,2,6-trimethyl-1,4-dihydropyridin-4-yl)furo[3,2-c]pyridin-4-yl]benzamide

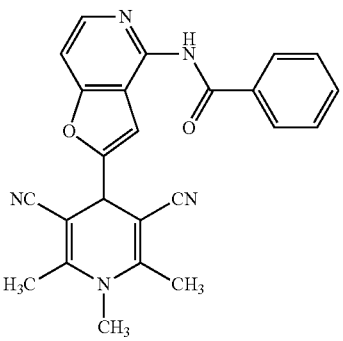 [SMILES: CC1=C(C#N)C(c2cc3c(NC(=O)c4ccccc4)nccc3o2)C(C#N)=C(C)N1C]

A solution of 100 mg (0.253 mmol) N-[2-(3,5-dicyano-2,6-dimethyl-1,4-dihydropyridin-4-yl)furo-[3,2-c]pyridin-4-yl]benzamide (Example 4) in DMF (1.4 ml) was cooled to 0° C., and 99 mg (0.30 mmol) caesium carbonate were added at this temperature. After stirring for 30 min, 19 μl (0.30 mmol) methyl iodide were added dropwise at room temperature, and the mixture was stirred at rt overnight. After this, additional methyl iodide (20 μL) was added, and stirring at rt was continued for further 48 h. The reaction mixture was then filtered, and the filtrate was directly purified by preparative RP-HPLC (acetonitrile/water+0.1% TFA, isocratic 40:60 v/v) to give 5.6 mg (5% of th.) of the title compound.

LC-MS (method 4): $R_t$=0.72 min; MS (ESIpos): m/z=410 (M+H)$^+$ $^1$H-NMR (400 MHz, acetonitrile-d$_3$): δ=8.24 (m, 1H), 8.15 (m, 2H), 8.04 (br. s, 1H), 7.66 (m, 1H), 7.56 (m, 3H), 7.04 (s, 1H), 4.81 (s, 1H), 4.13 (s, 3H), 2.09 (s, 6H) ppm.

The following compounds were prepared from the corresponding benzamides (Examples 11, 12, 14 and 16, respectively) in analogy to the procedure described in Example 5; purification was carried out by preparative RP-HPLC using an acetonitrile/water+0.1% TFA gradient.

| Example | Name/Structure (yield) | Analytical data |
|---|---|---|
| 18 | 4-(4-Aminofuro[3,2-c]pyridin-2-yl)-2,6-bis(difluoromethyl)-1,4-dihydropyridine-3,5-dicarbonitrile<br><br>(3% of th.)[1] | LC-MS (method 3):<br>$R_t$ = 1.24 min; m/z = 364 (M + H)$^+$<br>$^1$H-NMR (400 MHz, DMSO-d$_6$):<br>δ = 7.86 (d, 1H), 7.9-7.7 (br. s, 2H), 7.23 (s, 1H), 7.16 (d, 1H), 6.78 (t, 2H), 5.34 (s, 1H) ppm. |
| 19 | 8-(4-Aminofuro[3,2-c]pyridin-2-yl)-6-methyl-1,3,4,8-tetrahydropyrido[2,1-c]-[1,4]oxazine-7,9-dicarbonitrile<br><br>(18% of th.) | LC-MS (method 4):<br>$R_t$ = 0.57 min; m/z = 334 (M + H)$^+$<br>$^1$H-NMR (400 MHz, DMSO-d$_6$):<br>δ = 8.52 (br. s, 2H), 7.88 (d, 1H), 7.33 (d, 1H), 7.28 (s, 1H), 5.12 (s, 1H), 4.64-4.48 (m, 2H), 4.0-3.8 (m, 2H), 3.75-3.58 (m, 2H), 2.28 (s, 3H) ppm. |
| 20 | 4-(4-Aminofuro[3,2-c]pyridin-2-yl)-2-methyl-5-oxo-1,4,5,7-tetrahydrofuro[3,4-b]pyridine-3-carbonitrile<br><br>(4% of th.)[2] | LC-MS (method 4):<br>$R_t$ = 0.35 min; m/z = 309 (M + H)$^+$<br>$^1$H-NMR (400 MHz, DMSO-d$_6$):<br>δ = 10.32 (s, 1H), 7.74 (d, 1H), 6.85 (s, 1H), 6.75 (d, 1H), 6.45 (s, 2H), 4.92 (m, 2H), 4.88 (s, 1H), 2.13 (s, 3H) ppm. |

-continued

| Example | Name/Structure (yield) | Analytical data |
|---|---|---|
| 21 | 4-(4-Aminofuro[3,2-c]pyridin-2-yl)-2-(4-chlorophenyl)-5-oxo-1,4,5,7-tetrahydrofuro[3,4-b]pyridine-3-carbonitrile<br />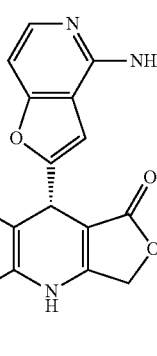<br />(10% of th.) | LC-MS (method 4):<br />$R_t$ = 0.70 min; m/z = 405 (M + H)$^+$<br />$^1$H-NMR (400 MHz, DMSO-$d_6$):<br />δ = 10.69 (s, 1H), 8.50 (br. s, 2H), 7.87 (d, 1H), 7.65 (m, 4H), 7.33 (d, 1H), 7.31 (s, 1H), 5.30 (s, 1H), 4.98 (m, 2H) ppm. |

[1] after further purification by preparative RP-HPLC [column: Sunfire C18, 5 μm, 19 mm × 150 mm; eluent: water/methanol/1% aq. ammonia, isocratic 56:30:14 v/v/v; flow rate: 25 ml/min; temperature: 40° C.; UV detection: 210 nm].

[2] after further purification by preparative thin layer chromatography (silica gel; eluent: dichloromethane/methanol + 0.1% triethylamine 10:1 v/v).

B. EVALUATION OF BIOLOGICAL ACTIVITY

Demonstration of the activity of the compounds of the present invention may be accomplished through in vitro, ex vivo, and in vivo assays that are well known in the art. For example, to demonstrate the activity of the compounds of the present invention, the following assays may be used.

c-Met Receptor Tyrosine Kinase Activity Assay (NADH Read-Out):

Recombinant human c-Met protein (Invitrogen, Carlsbad, Calif., USA) is used. As substrate for the kinase reaction the peptide KKKSPGEYVNIEFG (JPT, Germany) is used. For the assay, 1 μL of a 51-fold concentrated solution of the test compound in DMSO is pipetted into a white 384-well microtiter plate (Greiner Bio-One, Frickenhausen, Germany). 25 μL of a solution of c-Met (final concentration 30 nM) and pyruvate kinase/lactate dehydrogenase (Roche Diagnostics, Mannheim, Germany; final concentration 8 mg/L) in assay buffer [3-(N-morpholino)propanesulfonic acid (MOPS), 50 mM, pH 7; $MgCl_2$, 10 mM; bovine serum albumin (BSA), 0.01%; Triton X 100, 0.01%; DTT, 2 mM] are added, and the mixture is incubated for 5 min at room temperature. Then, the kinase reaction is started by the addition of 25 μL of a solution of adenosine triphosphate (ATP, final concentration 30 μM), substrate (final concentration 100 μM), nicotinamide adenine dinucleotide (NADH, final concentration 50 μM) and dithiothreitol (DTT, final concentration 2 mM) in assay buffer, and the resulting mixture is incubated for a reaction time of 100 min at 32° C.

Subsequently, the amount of phosphorylated substrate is evaluated by measurement of the decrease of NADH fluorescence. Therefore, the fluorescence emissions at 465 nm after excitation at 340 nm is measured in a fluorescence reader, e.g. Tecan Ultra (Tecan, Männedorf, Switzerland). The data are normalised (enzyme reaction without inhibitor=0% inhibition; all other assay components but no enzyme=100% inhibition). Normally, test compounds are tested on the same microtiter plate at 9 different concentrations in the range of 10 μM to 1 nM (10 μM, 3.1 μM, 1.0 μM, 0.3 μM, 0.1 μM, 0.03 μM, 0.01 μM, 0.003 μM, 0.001 μM; dilution series prepared before the assay at the level of the 51-fold concentrated stock solutions by serial 1:3 dilutions) in duplicate for each concentration, and $IC_{50}$ values are calculated using an inhouse software.

Compounds of the invention, when tested in this assay, demonstrated the ability to inhibit c-Met tyrosine kinase activity at $IC_{50}$ values of less than 10 μM, preferably at less than 1 μM.

Some representative $IC_{50}$ values are listed in the table below:

| Example No. | $IC_{50}$ [μM] |
|---|---|
| 5 | 0.023 |
| 6 | 0.037 |
| 10 | 0.043 |
| 14 | 0.142 |
| 19 | 0.61 |
| 21 | 0.26 | c-Met Receptor Tyrosine Kinase Homogeneous Time-Resolved Fluorescence Assay (Alternative Format):

The N-terminally His6-tagged recombinant kinase domain of the human c-Met (amino acids 960-1390), expressed in insect cells (SF21) and purified by Ni-NTA affinity chromatography and consecutive size exclusion chromatography (Superdex 200), is used. Alternatively, commercially available c-Met (Millipore) can be used. As substrate for the kinase reaction, the biotinylated poly-Glu,Tyr (4:1) copolymer (#61GT0BLC, Cis Biointernational, Marcoule, France) is used.

For the assay, 50 nL of a 100-fold concentrated solution of the test compound in DMSO is pipetted into a black low-volume 384-well microtiter plate (Greiner Bio-One, Frickenhausen, Germany). 2 μL of a solution of c-Met in assay buffer [25 mM Hepes/NaOH, pH 7.5; 5 mM $MgCl_2$; 5 mM $MnCl_2$; 2 mM dithiothreitol; 0.1% (v/v) Tween 20 (Sigma); 0.1% (w/v) bovine serum albumin] are added, and the mixture is incubated for 15 min at 22° C. to allow pre-binding of the test compound to the enzyme before the start of the kinase reaction. Then, the kinase reaction is started by the addition of 3 µL of a solution of adenosine triphosphate (ATP, 16.7 µM; final concentration in the 5 µL assay volume is 10 µM) and substrate (2.27 µg/mL, final concentration in the 5 µL assay volume is 1.36 µg/mL~30 nM) in assay buffer, and the resulting mixture is incubated for a reaction time of 30 min at 22° C. The concentration of c-Met in the assay is adjusted depending on the activity of the enzyme lot and is appropriately chosen to have the assay in the linear range; typical enzyme concentrations are in the range of about 0.03 nM (final concentration in the 5 µL assay volume). The reaction is stopped by the addition of 5 µL of a solution of HTRF detection reagents [40 nM streptavidine-XL ent and 2.4 nM PT66-Eu-chelate, an europium-chelate labelled anti-phosphotyrosine antibody (Perkin-Elmer)] in an aqueous EDTA solution [100 mM EDTA, 0.2% (w/v) bovine serum albumin in 50 mM HEPES/NaOH, pH 7.5].

The resulting mixture is incubated for 1 h at 22° C. to allow the binding of the biotinylated phosphorylated peptide to the streptavidine-XLent and the PT66-Eu-chelate. Subsequently, the amount of phosphorylated substrate is evaluated by measurement of the resonance energy transfer from the PT66-Eu-chelate to the streptavidine-XLent. Therefore, the fluorescence emissions at 620 nm and 665 nm after excitation at 350 nm are measured in an HTRF reader, e.g. Rubystar (BMG Lab-technologies, Offenburg, Germany) or Viewlux (Perkin-Elmer). The ratio of the emissions at 665 nm and at 622 nm is taken as the measure for the amount of phosphorylated substrate. The data are normalised (enzyme reaction without inhibitor=0% inhibition; all other assay components but no enzyme=100% inhibition). Normally, test compounds are tested on the same microtiter plate at 10 different concentrations in the range of 20 µM to 1 nM (20 µM, 6.7 µM, 2.2 µM, 0.74 µM, 0.25 µM, 82 nM, 27 nM, 9.2 nM, 3.1 nM and 1 nM; dilution series prepared before the assay at the level of the 100-fold concentrated stock solutions by serial 1:3 dilutions) in duplicate for each concentration, and $IC_{50}$ values are calculated by a 4-parameter-fit using an inhouse software.

Compounds of the invention, when tested in this assay, demonstrated the ability to inhibit c-Met tyrosine kinase activity at $IC_{50}$ values of less than 10 µM, preferably at less than 1 µM.

Some representative $IC_{50}$ values are listed in the table below:

| Example No. | $IC_{50}$ [µM] |
|---|---|
| 6 | 0.057 |
| 18 | 1.03 |

Phospho-c-Met Assay:

This is a cell based, ELISA-like assay [Meso Scale Discovery (MSD), Gaithersburg, Md., USA] using MKN-45 tumor cells (gastric carcinoma, purchased from ATCC) without growth factor stimulation. The cells are plated in full growth media (10 000 cells/well) in 96-well plates on day one. On day two, after a two-hour drug treatment in serum-free media, cells are washed and then lysed (60 µl/well using MSD recommended lysis buffer) and frozen at −80° C. Also on day two, non-specific antibody-binding sites on the MSD phospho-Met plates are blocked with MSD Blocking Solution A overnight at 4° C. On day three, frozen lysates are thawed on ice, and 25 µl of lysate is transferred to the MSD phospho-Met plate, for 1 hour with shaking, after washing once with Tris-buffered saline+0.05% Tween 20 (TBST). After removing the unbound proteins, the Sulfa-TAG anti-Met antibody from MSD is added at a final concentration of 5 nM in antibody dilution buffer (following protocol of MSD) to the plate for 1 hour with shaking. The plate is then washed with TBST buffer three times before adding 1× MSD Read Buffer. The plate is then read on the MSD Discovery Workstation instrument. Raw data, including wells with 10 µM of a reference compound (minimum signal), and DMSO wells without any drug treatment (maximum signal), are entered into the Analyze 5 program for $IC_{50}$ value determinations.

Cellular Phospho-c-Met Assay:

Human gastric adenocarcinoma cells (MKN45, purchased from ATCC) seeded on 384-well microtiter plates (9000 cells/well) are incubated in 25 µl full growth media for 24 h at 37° C. with 5% $CO_2$. On day two, after a two-hour drug treatment in serum-reduced media containing 0.1% FCS, cells are washed and lysed. Lysates are transferred to BSA-blocked plates with prebound c-Met capture antibody [purchased from Mesoscale Discovery (MSD), Gaithersburg, Md., USA] for 1 hour with shaking, after washing once with Tris-buffered saline+0.05% Tween 20 (TBST). Following the MSD protocol, the Sulfa-TAG anti-phospho-c-Met detection antibody is added at a final concentration of 5 nM in antibody dilution buffer to the plate for 1 hour with shaking at RT. After washing the wells with Tris buffer, 1× reading buffer is added, and the plates are measured on the Sector Imager 6000 (purchased from Mesoscale). $IC_{50}$ values are calculated from dose-response curves using Marquardt-Levenberg-Fit.

In-Vitro Tumor Cell Proliferation Assay:

The adherent tumor cell proliferation assay used to test the compounds of the present invention involves a read-out called Cell Titre-Glo developed by Promega [B A Cunningham, "A Growing Issue: Cell Proliferation Assays. Modern kits ease quantification of cell growth", *The Scientist* 2001, 15 (13), 26; S. P. Crouch et al., "The use of ATP bioluminescence as a measure of cell proliferation and cytotoxicity", *Journal of Immunological Methods* 1993, 160, 81-88]. Generation of a luminescent signal corresponds to the amount of ATP present, which is directly proportional to the number of metabolically active (proliferating) cells.

H460 cells (lung carcinoma, purchased from ATCC) are plated in 96-well plates at 3000 cells/well in complete media with 10% fetal calf serum and incubated 24 hours at 37° C. Twenty-four hours after plating, test compounds are added over a final concentration range of 10 nM to 20 µM in serial dilutions at a final DMSO concentration of 0.2%. Cells are incubated for 72 hours at 37° C. in complete growth media after addition of the test compound. On day 4, using a Promega Cell Titre-Glo Luminescent® assay kit, the cells are lysed, and 100 µl of substrate/buffer mixture is added to each well, mixed and incubated at room temperature for 8 minutes. The samples are read on a luminometer to measure the amount of ATP present in the cell lysates from each well, which corresponds to the number of viable cells in that well. Values read at 24-hour incubation are subtracted as Day 0. For determination of $IC_{50}$ values, a linear regression analysis can be used to determine the drug concentration which results in a 50% inhibition of cell proliferation using this assay format. This protocol can be applied to different cell lines of interest, which include, but not limited to, CAKI-1, MNK-45, GTL-16, HCC2998, K562, H441, K812, MEG01, SUP15 and HCT116.

Although the invention has been disclosed with reference to specific embodiments, it is apparent that other embodiments and variations of the invention may be devised by others skilled in the art without departing from the true spirit and scope of the invention. The claims are intended to be construed to include all such embodiments and equivalent variations.

C. EXAMPLES RELATING TO PHARMACEUTICAL COMPOSITIONS

Pharmaceutical compositions according to the present invention can be illustrated as follows:

Sterile i.v. Solution:

A 5 mg/ml solution of the desired compound of this invention can be made using sterile, injectable water, and the pH is adjusted if necessary. The solution is diluted for administration to 1-2 mg/ml with sterile 5% dextrose and is administered as an i.v. infusion over about 60 minutes.

Lyophilized Powder for i.v. Administration:

A sterile preparation can be prepared with (i) 100-1000 mg of the desired compound of this invention as a lyophilized powder, (ii) 32-327 mg/ml sodium citrate, and (iii) 300-3000 mg Dextran 40. The formulation is reconstituted with sterile, injectable saline or 5% dextrose to a concentration of 10 to 20 mg/ml, which is further diluted with saline or 5% dextrose to 0.2 to 0.4 mg/ml, and is administered either as i.v. bolus or by i.v. infusion over 15-60 minutes.

Intramuscular Suspension:

The following solution or suspension can be prepared for intramuscular injection:

50 mg/ml of the desired, water-insoluble compound of this invention; 5 mg/ml sodium carboxymethylcellulose; 4 mg/mL TWEEN 80; 9 mg/ml sodium chloride; 9 mg/ml benzyl alcohol.

Hard Shell Capsules:

A large number of unit capsules are prepared by filling standard two-piece hard galantine capsules each with 100 mg of powdered active ingredient, 150 mg of lactose, 50 mg of cellulose and 6 mg of magnesium stearate.

Soft Gelatin Capsules:

A mixture of active ingredient in a digestible oil such as soybean oil, cottonseed oil or olive oil is prepared and injected by means of a positive displacement pump into molten gelatin to form soft gelatin capsules containing 100 mg of the active ingredient. The capsules are washed and dried. The active ingredient can be dissolved in a mixture of polyethylene glycol, glycerin and sorbitol to prepare a water-miscible medicine mix.

Tablets:

A large number of tablets are prepared by conventional procedures so that the dosage unit is 100 mg of active ingredient, 0.2 mg of colloidal silicon dioxide, 5 mg of magnesium stearate, 275 mg of microcrystalline cellulose, 11 mg of starch, and 98.8 mg of lactose. Appropriate aqueous and non-aqueous coatings may be applied to increase palatability, improve elegance and stability, or delay absorption.

We claim:
1. A compound of formula (I)

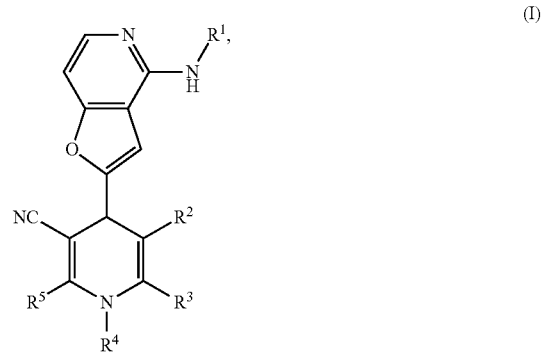

wherein
$R^1$ is hydrogen, $(C_1-C_6)$-alkyl, $(C_1-C_6)$-alkylcarbonyl, benzyl or benzoyl,
wherein the phenyl part of said benzyl and benzoyl groups, respectively, may be substituted with one or two residues independently selected from the group consisting of fluoro, chloro, bromo, cyano, methyl, difluoromethyl, trifluoromethyl, ethyl, methoxy, difluoromethoxy and trifluoromethoxy,
$R^2$ is cyano,
$R^3$ is $(C_1-C_4)$-alkyl optionally substituted with up to three fluoro atoms,
or
$R^2$ and $R^3$ are joined and, taken together with the carbon atoms to which they are attached, form a fused ring of the formula

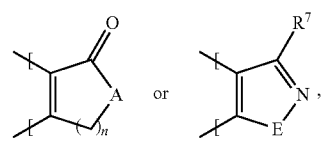

wherein
n is an integer of 1 or 2,
A is —$CH_2$—, —O— or —$NR^6$—, wherein
$R^6$ is hydrogen or $(C_1-C_4)$-alkyl,
E is —O—, —NH— or —$NCH_3$—,
and
$R^7$ is hydrogen or methyl,
$R^4$ is hydrogen, $(C_1-C_4)$-alkyl or cyclopropyl,
$R^5$ is $(C_1-C_6)$-alkyl optionally substituted with up to three fluoro atoms,
or
is phenyl or pyridyl each of which may be substituted with one or two residues independently selected from the group consisting of fluoro, chloro, bromo, cyano, methyl, difluoromethyl, trifluoromethyl, ethyl, methoxy, difluoromethoxy and trifluoromethoxy,
or
$R^4$ and $R^5$ are joined and, taken together with the nitrogen and the carbon atom to which they are attached, form a fused ring of the formula

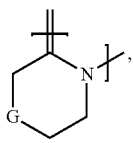

wherein
G is —CH$_2$— or —O—,
or a pharmaceutically acceptable salt, hydrate and/or solvate thereof.

2. The compound of formula (I) according to claim 1, wherein
R$^1$ is hydrogen, methyl, acetyl or benzoyl,
R$^2$ is cyano,
R$^3$ is methyl, difluoromethyl or trifluoromethyl,
or
R$^2$ and R$^3$ are joined and, taken together with the carbon atoms to which they are attached, form a fused ring of the formula

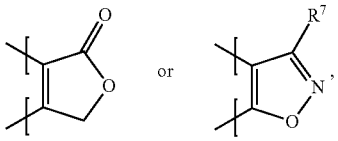

wherein
R$^7$ is hydrogen or methyl,
R$^4$ is hydrogen or methyl,
R$^5$ is (C$_1$-C$_4$)-alkyl optionally substituted with up to three fluoro atoms,
or
is phenyl optionally substituted with one or two residues independently selected from the group consisting of fluoro, chloro, methyl and trifluoromethyl,
or
R$^4$ and R$^5$ are joined and, taken together with the nitrogen and the carbon atom to which they are attached, form a fused morpholine ring of the formula

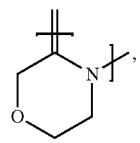

or a pharmaceutically acceptable salt, hydrate and/or solvate thereof.

3. The compound of formula (I) according to claim 1, wherein
R$^1$ is hydrogen or benzoyl,
R$^2$ is cyano,
R$^3$ is methyl, difluoromethyl or trifluoromethyl,
or
R$^2$ and R$^3$ are joined and, taken together with the carbon atoms to which they are attached, form a fused lactone ring of the formula

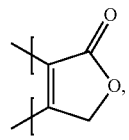

R$^4$ is hydrogen,
and
R$^5$ is methyl, difluoromethyl or trifluoromethyl, or is phenyl optionally substituted with fluoro or chloro,
or a pharmaceutically acceptable salt, hydrate and/or solvate thereof.

4. A pharmaceutical composition comprising a compound as defined in claim 1, or a pharmaceutically acceptable salt, hydrate and/or solvate thereof, and a pharmaceutically acceptable excipient.

* * * * *